United States Patent
Justin et al.

(10) Patent No.: US 10,716,643 B2
(45) Date of Patent: Jul. 21, 2020

(54) SURGICAL PROJECTION SYSTEM AND METHOD

(71) Applicant: OrbisMV LLC, Orlando, FL (US)

(72) Inventors: Daniel F. Justin, Orlando, FL (US); Ronald A. Tetenbaum, Winter Park, FL (US); Jason M. Eichenholz, Winter Park, FL (US); Eric J. Tetenbaum, Winter Park, FL (US)

(73) Assignee: ORBISMV LLC, Orlando, FL (US)

(*) Notice: Subject to any disclaimer, the term of this patent is extended or adjusted under 35 U.S.C. 154(b) by 222 days.

(21) Appl. No.: 15/973,515

(22) Filed: May 7, 2018

(65) Prior Publication Data

US 2018/0325618 A1    Nov. 15, 2018

Related U.S. Application Data

(60) Provisional application No. 62/502,542, filed on May 5, 2017.

(51) Int. Cl.
*A61B 34/10* (2016.01)
*A61B 90/00* (2016.01)
(Continued)

(52) U.S. Cl.
CPC .............. *A61B 90/37* (2016.02); *A61B 34/10* (2016.02); *A61B 34/20* (2016.02); *A61B 90/36* (2016.02);
(Continued)

(58) Field of Classification Search
CPC ..... A61B 90/00; A61B 90/37; A61B 17/1703; A61B 17/1764; A61B 17/17; A61V 34/10; A61V 34/20
See application file for complete search history.

(56) References Cited

U.S. PATENT DOCUMENTS

| 2008/0077158 A1 | 3/2008 | Haider et al. |
| 2013/0060146 A1* | 3/2013 | Yang .................... A61B 5/055 600/476 |

(Continued)

OTHER PUBLICATIONS

Jacques et al. "Polarized Light Imaging of Tissues", Lasers and Current Optical Techniques in Biology 4, Ch. 19 (2004): 591-607.

(Continued)

*Primary Examiner* — Christopher J Beccia
(74) *Attorney, Agent, or Firm* — David Meibos; Maywood IP Law

(57) ABSTRACT

Systems and methods for guiding a surgical procedure based on a surgical procedure plan may include an image capture device that captures one or more images of an exposed anatomical feature of a patient. These systems and methods may also include a computing device configured to receive a surgical procedure plan based on one or more desired attributes related to an anatomical 3D model representing the exposed anatomical feature of the patient. The computing device may register the anatomical 3D model to the exposed anatomical feature of the patient based on the one or more images of the exposed anatomical feature and a projector may further provide surgical guidance information to a surgeon based on the surgical procedure plan to facilitate performance of the surgical procedure.

20 Claims, 9 Drawing Sheets

(51) Int. Cl.
*A61B 34/20* (2016.01)
*G16H 20/40* (2018.01)
*G16H 30/40* (2018.01)
*G16H 50/50* (2018.01)
*A61B 17/17* (2006.01)
*A61B 90/13* (2016.01)
*A61B 90/50* (2016.01)

(52) U.S. Cl.
CPC ............ *G16H 20/40* (2018.01); *G16H 30/40* (2018.01); *G16H 50/50* (2018.01); *A61B 17/1703* (2013.01); *A61B 17/1764* (2013.01); *A61B 90/13* (2016.02); *A61B 2034/104* (2016.02); *A61B 2034/105* (2016.02); *A61B 2034/2048* (2016.02); *A61B 2034/2051* (2016.02); *A61B 2034/2057* (2016.02); *A61B 2090/365* (2016.02); *A61B 2090/366* (2016.02); *A61B 2090/367* (2016.02); *A61B 2090/3612* (2016.02); *A61B 2090/371* (2016.02); *A61B 2090/372* (2016.02); *A61B 2090/373* (2016.02); *A61B 2090/376* (2016.02); *A61B 2090/502* (2016.02)

(56) References Cited

U.S. PATENT DOCUMENTS

2014/0107471 A1  4/2014  Haider et al.
2016/0022374 A1  1/2016  Haider et al.
2017/0312035 A1* 11/2017  May ...................... A61B 34/20

OTHER PUBLICATIONS

Li "Time of Flight Camera—An Introduction", Technical White Paper, SLOA190B, Jan. 2014 (10 pp).

Ramella-Roman et al. "Polarized light imaging with a hand-held camera", Saratov Fall Meeting 2002: Optical Technologies in Biophysics and Medicine IV. vol. 5068. International Society for Optics and Photonics, 2003.

* cited by examiner

SURGICAL PROJECTION SYSTEM AND METHOD

CROSS-REFERENCE TO RELATED APPLICATIONS

The present application claims the benefit of U.S. Provisional Patent Application Ser. No. 62/502,542, entitled SURGICAL PROJECTION SYSTEM AND METHOD, which was filed on May 5, 2017. The above-referenced application is incorporated by reference herein as though set forth herein in its entirety.

TECHNICAL FIELD

The present disclosure relates to surgical guidance systems and methods. More specifically, the present disclosure relates to surgical guidance systems and methods utilizing visual guidance information that is based on a surgical procedure plan.

BACKGROUND

Many orthopedic surgeries are complex events with several steps. The need for precise alignment and placement of components often requires the surgeon to take several measurements and/or use several different resection guides and other instruments to ensure that components are properly placed. The resulting surgery can be very long, and each step may introduce additional potential for errors.

For example, total knee replacement ("TKR") surgical procedures are complex and require numerous cutting and alignment jigs to perform accurate tissue resections. Preparing and placing cutting and alignment jigs is often the most significant part of the TKR procedure, often introducing errors in the TKR procedure.

This is important because the TKR prosthesis must be accurately implanted to ensure that the joint surfaces of the TKR prosthesis are properly aligned. If the alignment is inaccurate, this misalignment can compromise function of the TKR joint and eventually lead to failure, requiring a major revision to the TKR joint that will most likely be costly and time consuming.

A surgeon may use a variety of jigs to guide the cutting of femoral, tibial, and/or patellar bones. These jigs are complex and expensive devices that require significant time and skill to properly locate and attach to the patient so accurate resections to the femoral, tibial, and/or patellar bones may be made. Accordingly, systems and methods that reduce this complexity and expense in TKR surgical procedures would be very desirable.

SUMMARY

The various systems and methods of the present disclosure have been developed in response to the present state of the art, and in particular, in response to the problems and needs in the art that have not yet been fully solved by currently available technology.

In some embodiments, a system for guiding a surgical procedure based on a surgical procedure plan may include an image capture device that captures one or more images of an exposed anatomical feature of a patient at a surgical site. The system may also include a computing device configured to receive a surgical procedure plan that may be based on one or more desired attributes related to an anatomical 3D model that represents the exposed anatomical feature of the patient at the surgical site. The computing device may also be configured to register the anatomical 3D model to the exposed anatomical feature of the patient based on images of the exposed anatomical feature. In addition, the system may also include a projector that provides guidance information to the surgeon based on the surgical procedure plan to facilitate performance of the surgical procedure at the surgical site by the surgeon.

In other embodiments, a method for guiding a surgical procedure based on a surgical procedure plan may include receiving a surgical procedure plan based on one or more desired attributes related to an anatomical 3D model representing an anatomical feature of a patient at a surgical site. The method may also include capturing at least one image of an exposed anatomical feature of the patient at the surgical site and registering the anatomical 3D model to the exposed anatomical feature of the patient at the surgical site. The method may further include providing guidance information to a surgeon based on the surgical procedure plan to facilitate performance of the surgical procedure at the surgical site by the surgeon.

In yet other embodiments, a method for creating a surgical procedure plan may include receiving anatomical data indicative of an anatomical feature of a patient at a surgical site and constructing an anatomical 3D model based on the anatomical data that represents the anatomical feature of the patient at the surgical site. The method may also include projecting an image of the anatomical 3D model on a head-mounted display unit coupled to a surgeon, such that the projected image of the anatomical 3D model is displayed within a surgeon's field-of-view on the head-mounted display unit. The method may further include sensing one or more commands issued by the surgeon relative to the anatomical 3D model and manipulating one or more attributes related to the anatomical 3D model based on the one or more commands issued by the surgeon. The method may additionally include selecting one or more desired attributes related to the anatomical 3D model for inclusion in a surgical procedure plan and creating the surgical procedure plan based on the selected one or more desired attributes related to the anatomical 3D model.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

It is to be understood that the drawings are for purposes of illustrating the concepts of the disclosure and are not to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, systems, and methods, as represented in the Figures, is not intended to limit the scope of the disclosure, as claimed, but is merely representative of exemplary embodiments of the disclosure.

Figure 1:
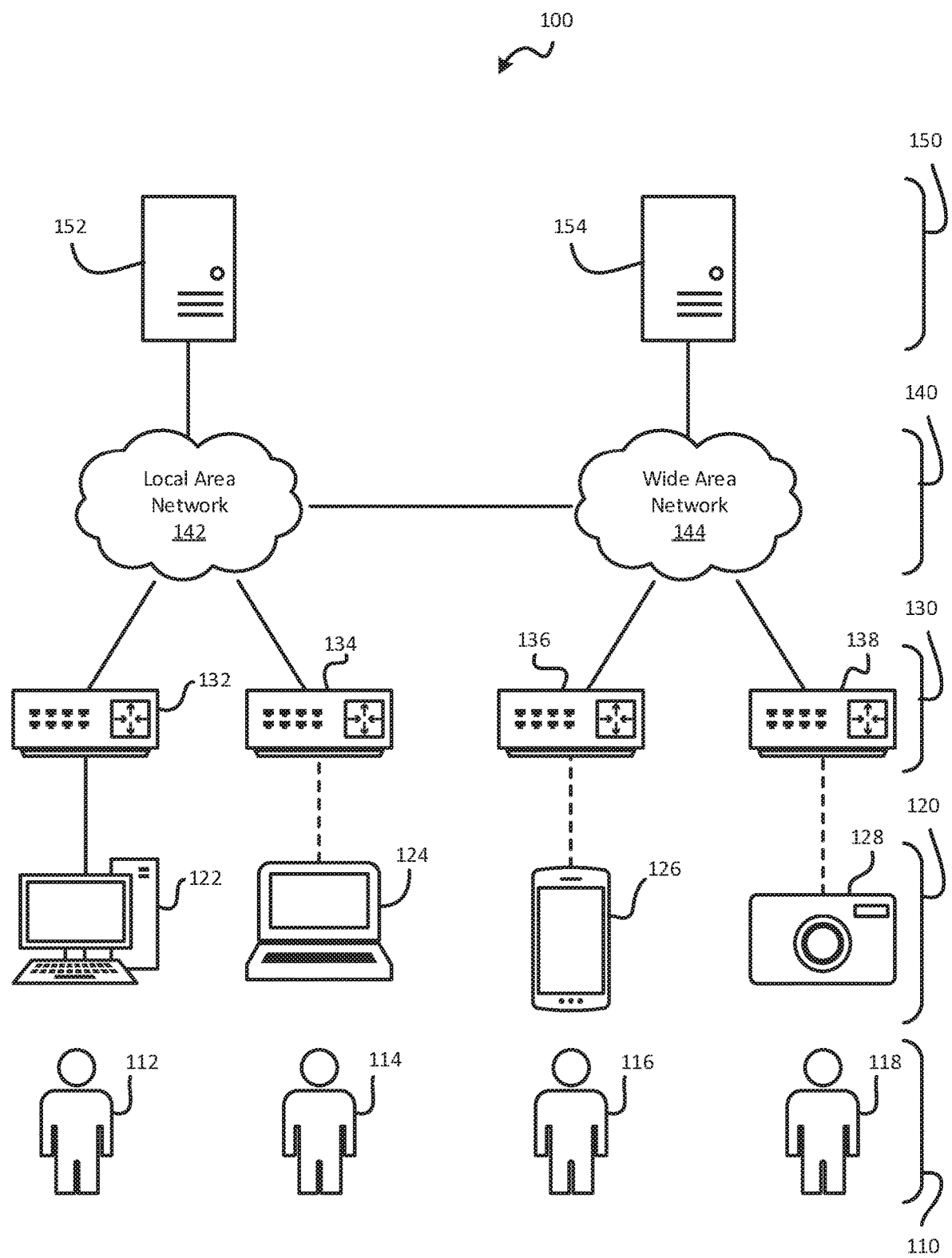
FIG. 1 is a schematic block diagram illustrating a system, according to one embodiment of the disclosure.

Referring to FIG. 1, a schematic block diagram illustrates a system 100 according to one embodiment. The system 100 may be used for the benefit of one or more users 110, which may include a first user 112, a second user 114, a third user 116, and a fourth user 118 as shown in FIG. 1. Each of the users 110 may use one of a variety of computing devices 120, which may include any of a wide variety of devices that carry out computational steps, including but not limited to a desktop computer 122 used by the first user 112, a laptop computer 124 used by the second user 114, a smartphone 126 used by the third user 116, a camera 128 used by the fourth user 118, and the like. The system and method presented herein may be carried out on any type of computing device.

The computing devices 120 may optionally be connected to each other and/or other resources. Such connections may be wired or wireless, and may be implemented through the use of any known wired or wireless communication standard, including but not limited to Ethernet, 802.11a, 802.11b, 802.11g, and 802.11n, universal serial bus (USB), Bluetooth, cellular, near-field communications (NFC), Bluetooth Smart, ZigBee, and the like. In FIG. 1, by way of example, wired communications are shown with solid lines and wireless communications are shown with dashed lines.

Communications between the various elements of FIG. 1 may be routed and/or otherwise facilitated through the use of routers 130. The routers 130 may be of any type known in the art, and may be designed for wired and/or wireless communications through any known communications standard including but not limited to those listed above. The routers 130 may include, for example, a first router 132 that facilitates communications to and/or from the desktop computer 122, a second router 134 that facilitates communications to and/or from the laptop computer 124, a third router 136 that facilitates communications to and/or from the smartphone 126, and a fourth router 138 that facilitates communications to and/or from the camera 128.

The routers 130 may facilitate communications between the computing devices 120 and one or more networks 140, which may include any type of networks including but not limited to local area networks such as a local area network 142, and wide area networks such as a wide area network 144. In one example, the local area network 142 may be a network that services an entity such as a business, non-profit entity, government organization, or the like. The wide area network 144 may provide communications for multiple entities and/or individuals, and in some embodiments, may be the Internet. The local area network 142 may communicate with the wide area network 144. If desired, one or more routers or other devices may be used to facilitate such communication.

The networks 140 may store information on servers 150 or other information storage devices. As shown, a first server 152 may be connected to the local area network 142, and may thus communicate with devices connected to the local area network 142 such as the desktop computer 122 and the laptop computer 124. A second server 154 may be connected to the wide area network 144, and may thus communicate with devices connected to the wide area network 144, such as the smartphone 126 and the camera 128. If desired, the second server 154 may be a web server that provides web pages, web-connected services, executable code designed to operate over the Internet, and/or other functionality that facilitates the provision of information and/or services over the wide area network 144.

Figure 2A:
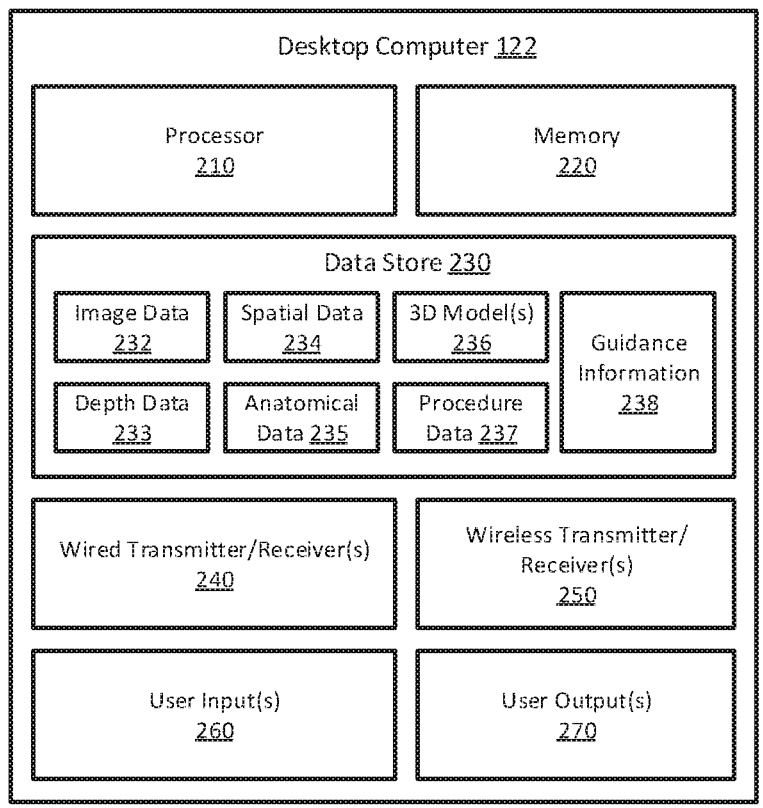
FIG. 2A is a schematic block diagram illustrating a computing device which is capable of practicing the disclosure in a standalone computing environment, according to one embodiment of the disclosure.

Referring to FIG. 2A, a schematic block diagram illustrates an exemplary computing device of the computing devices 120 that may enable implementation of the methods of the present disclosure in a standalone computing environment. The computing device 120 may be, for example, the desktop computer 122 of FIG. 1.

As shown, the desktop computer 122 may include a processor 210 that is designed to execute instructions on data. The processor 210 may be of any of a wide variety of types, including microprocessors with x86-based architecture or other architecture known in the art, application-specific integrated circuits (ASICs), field-programmable gate arrays (FPGA's), and the like. The processor 210 may optionally include multiple processing elements, or "cores." The processor 210 may include a cache that provides temporary storage of data incident to the operation of the processor 210.

The desktop computer 122 may further include memory 220, which may be volatile memory such as random access memory (RAM). The memory 220 may include one or more memory modules. The memory 220 may include executable instructions, data referenced by such executable instructions, and/or any other data that may beneficially be made readily accessible to the processor 210.

The desktop computer 122 may further include a data store 230, which may be non-volatile memory such as a hard drive, flash memory, and/or the like. The data store 230 may include one or more data storage elements. The data store 230 may store executable code such as an operating system and/or various programs to be run on the desktop computer 122. The data store 230 may further store data to be used by such programs. For the system and method of the present disclosure, the data store 230 may store image data 232, depth data 233, spatial data 234, anatomical data 235, one or more 3D models 236, procedure data 237, and/or guidance information 238.

The image data 232 may include one or more images captured by one or more image capture devices. The image data 232 may include visual images, such as images in RGB, HSI, and/or any other known scheme of visual color. Additionally or alternatively, the image data 232 may include images generated from receipt of electromagnetic energy invisible and/or visible to the human eye, including but not limited to infrared, radio, ultraviolet, microwave, X, and Gamma radiation. Thus, the image data 232 may include any mapping of electromagnetic energy received by one or more sensors, applied across any number of dimensions.

The depth data 233 may include data indicative of the depth of one or more objects appearing in the image data, which may be captured by one or more image capture devices and/or depth capture devices. For example, the depth data 233 may include one or more depth maps, each of which may correspond to one of the images of the image data 232, and may indicate the depth of objects and/or features appearing in the image. The depth data 233 may exist in any format capable of expressing the relative depth of objects from a sensor such as an image capture device and/or depth capture device.

The spatial data 234 may be indicative of the relative positions and/or orientations of objects in an environment. For example, the spatial data 234 may indicate the location and/or orientation of a sensor or projector relative to a surgical instrument, a patient, objects in the operating room, etc. Spatial data may be obtained from one or more sensors that detect the relative positions and/or orientations of objects. In some embodiments, such sensors may read the positions and/or orientations of passive devices such as radio frequency identification (RFID) tags and the like.

By way of example, RFID tags, active fiducial markers, and/or passive fiducial markers may be placed on objects such as a sensor, projector, instrument, implant, patient, exposed anatomical feature of the patient, etc. The positions and/or orientations of the RFID tags, active fiducial markers, and/or passive fiducial markers may then be read by a sensor that receives radio frequency electromagnetic energy to determine the positions and/or orientations of the RFID tags, active fiducial markers, and/or passive fiducial markers.

In other embodiments, a light detection and ranging ("LiDAR") system which generate point cloud data through the use of a rotatable pulsing laser rangefinder may be used to create a 3D map of an exposed anatomical feature of the patient with point cloud data. The point cloud data may be considered an "image," and may be used as a depth map indicative of the depth of points on an object surface from the LiDAR sensor. Thus, the output from the LiDAR sensor may be a form of the image data 232 and/or the depth data 233.

As opposed to passive sensors which may detect energy naturally emitted from an object, LiDAR uses active sensors emitting their own energy source for illumination of the object. The energy emitted from the energy source in a LiDAR system may strike a target object, reflect off the target object, and then be detected/measured by LiDAR receiver sensors. Thus, LiDAR is an example of an active sensor utilizing laser (Light Amplification by Stimulated Emission of Radiation) to transmit a light pulse in combination with a receiver including sensitive detectors to measure the backscattered/reflected light from a target object. The distance to the target object may then be determined by recording the time between transmission of the laser light and the return of backscattered pulses from the target object in view of the speed of light, which may be used to calculate the distance traveled by the LiDAR light. Thus, LiDAR is a surveying and/or 3D mapping method that measures distance to a target object by illuminating the target with pulsed laser light and measuring the reflected pulses with a sensor. Differences in laser return times and/or wavelengths may also be used to make digital 3D models representing a target object. LiDAR may also be referred to as "laser scanning" and/or "3D scanning." LiDAR lasers may utilize any of: ultraviolet, visible, near infrared, infrared, far infrared, and/or radio wave electromagnetic radiation/light in order to image objects. Narrow laser beams and/or laser beams utilizing high frequency electromagnetic radiation may also be used with LiDAR techniques to map physical features with very high resolutions. LiDAR light may be reflected off an object via a backscattering process. Different types of backscattering may be used in LiDAR applications and may include, but not limited to: Rayleigh scattering, Mie scattering, Raman scattering, fluorescence, etc. Suitable combinations of wavelengths may also allow for remote mapping of a target object by identifying wavelength-dependent changes in the intensity of the returned, backscattered signal.

In general, two kinds of LiDAR detection systems may include "incoherent" or "direct energy" detection (which may principally measure amplitude changes of the reflected light), and "coherent" detection (which may measure Doppler shifts or other changes in the phase of the reflected light). Coherent systems may use optical heterodyne detection, which may be more sensitive than direct detection and may operate at a much lower power. In both coherent and incoherent LiDAR, there may be two types of laser pulse systems: micropulse LiDAR systems and high-power LiDAR systems. Micropulse LiDAR systems may utilize intermittent bursts of laser energy to save laser energy and be more "eye-safe" than high-power LiDAR systems (e.g., micropulse LiDAR systems may be used without the need for eye-safety precautions).

LiDAR system may include several major components such as a laser, a scanner/optics, a photodetector, receiver electronics, and a position/navigation system. LiDAR Laser settings may include a laser repetition rate (which may control the data collection speed), a pulse length (which may generally be determined by an attribute of the laser cavity length), a number of passes required through a gain material, and Q-switch or "pulsing speed." Better target resolution may be achieved with shorter pulses. However, the LiDAR receiver, detectors, and/or electronics may need to have sufficient bandwidth in order to detect shorter pulses. How quickly images may be developed from LiDAR scans may be dependent on the speed at which LiDAR images are scanned. LiDAR images may be scanned in the azimuth and/or elevation directions with dual oscillating plane mirrors, or with a combination a polygon mirror and a dual axis scanner. Different optics may also affect the angular resolution and/or range that may be detected with a LiDAR. Moreover, LiDAR images may also be collected with a hole-mirror and/or a beam splitter in order to collect a LiDAR return signal. LiDAR photodetector technologies may include solid state photodetectors (such as silicon avalanche photodiodes, as one example) and/or photomultipliers. LiDAR sensors that are mounted on mobile platforms may also require additional instrumentation that determines the absolute position and/or orientation of the LiDAR sensor (e.g., a Global Positioning System receiver, an Inertial Measurement Unit (IMU), and the like). Moreover, LiDAR 3D imaging can be achieved using both scanning and non-scanning LiDAR systems. For example, "3D gated viewing laser radar" is a non-scanning laser ranging system that may utilize a pulsed laser and a fast gated camera. Imaging LiDAR may also be performed using arrays of high speed detectors and modulation sensitive detector arrays, which may be formed on a single silicon chip using Complementary Metal Oxide Semiconductor (CMOS) and/or hybrid CMOS/Charge-coupled device (CCD) fabrication techniques. In these devices, each pixel detector may perform local processing such as demodulation, gating at high speed, and/or down converting of the signals to a suitable videorate, such that the array of high speed detectors may be read like a camera. Using this technique many thousands of pixels/channels may be acquired simultaneously. High resolution 3D LiDAR cameras may also use "homodyne detection" with an electronic CCD or CMOS shutter. A coherent imaging LiDAR may also use a "synthetic array heterodyne detection" to enable a "staring single element receiver" to act as though it were an imaging array.

The anatomical data 235 may provide details regarding the anatomy of a patient. For example, for orthopedic procedures, the anatomical data 235 may provide the dimensions of one or more bones involved in a surgical procedure, data regarding the quality, porosity, or other characteristics of the bone, and/or the like. The anatomical data 235 may be obtained by processing other data, such as the image data 232, the depth data 233, and/or the spatial data 234, or may be obtained directly by scans of the surgical site, such as CT scans, MRI scans, MRT scans, 2D x-ray scans, 3D x-ray scans, fluoroscopy, and the like.

The anatomical 3D models, or 3D models 236, may be models of anatomical features of the surgical site. For example, for an orthopedic procedure, the 3D models 236 may include one or more models of bone surfaces involved in the surgical procedure. The 3D models 236 may be obtained from other data, such as the image data 232, the depth data 233, the spatial data 234, and/or the anatomical data 235.

The procedure data 237 may be data regarding the specific surgical procedure to be performed on the patient. For example, for a knee replacement, the procedure data 237 may include data regarding specific drilling locations and orientations, specific bone resections to be made, bone preparation steps, and/or other instrument manipulations needed to properly attach the implant(s) to the bone(s). The procedure data 237 may include, in the example of a knee replacement, the specific location, orientation, and size of drill holes and/or cuts to be made in the tibia and/or femur. The procedure data 237 may be obtained, for example, from a method form planning a surgical procedure, as will be discussed in more detail below. The procedure data 237 may also include data from one or more databases of surgical procedures, implants, instruments, etc. For example, manufacturers may provide databases that describe certain characteristics relating to their implants and/or surgical instruments. Thus, the procedure data 237 may include patient-specific data, as well as non-patient-specific data.

The guidance information 238 may be information that can be presented to a practitioner, such as a surgeon, to provide guidance regarding how the surgical procedure should be carried out. The guidance information 238 may be patient-specific, and may be generated through use of the models 236 and the procedure data 237. The guidance information 238 may further include information regarding how to move one or more instruments to perform the desired procedure. In the case of a knee replacement, the guidance information 238 may include the locations, orientations, and/or sizes of access points to the surgical site and/or within specific tissues at the surgical site, bone resections, holes to be reamed or otherwise formed in bone, the specific implant(s) and/or instrument size(s) and/or type(s) to be used, and/or the locations, orientations, or sizes of the implants as they will appear after implantation is complete. The guidance information may be projected directly onto the surgical site and/or projected in an augmented/virtual reality environment in order to provide guidance to the surgeon during performance of the surgical procedure.

The desktop computer 122 may further include one or more wired transmitter/receivers 240, which may facilitate wired communications between the desktop computer 122 and any other device, such as the other computing devices 120, the servers 150, and/or the routers 130 of FIG. 1. The wired transmitter/receivers 240 may communicate via any known wired protocol, including but not limited to any of the wired protocols described in FIG. 1. In some embodiments, the wired transmitter/receivers 240 may include Ethernet adapters, universal serial bus (USB) adapters, and/or the like.

The desktop computer 122 may further include one or more wireless transmitter/receivers 250, which may facilitate wireless communications between the desktop computer 122 and any other device, such as the other computing devices 120, the servers 150, and/or the routers 130 of FIG. 1. The wireless transmitter/receivers 250 may communicate via any known wireless protocol, including but not limited to any of the wireless protocols described in FIG. 1. In some embodiments, the wireless transmitter/receivers 250 may include Wi-Fi adapters, Bluetooth adapters, cellular adapters, and/or the like.

The desktop computer 122 may further include one or more user inputs 260 that receive input from a user such as the third user 116 of FIG. 1. The user inputs 260 may be integrated into the desktop computer 122, or may be separate from the desktop computer 122 and connected to it by a wired or wireless connection, which may operate via the wired transmitter/receivers 240 and/or the wireless transmitter/receivers 250. The user inputs 260 may include elements such as a touch screen, buttons, keyboard, mouse, trackball, track pad, stylus, digitizer, digital camera, microphone, and/or other user input devices known in the art.

The desktop computer 122 may further include one or more user outputs 270 that provide output to a user such as the third user 116 of FIG. 1. The user outputs 270 may be integrated into the desktop computer 122, or may be separate from the desktop computer 122 and connected to it by a wired or wireless connection, which may operate via the wired transmitter/receivers 240 and/or the wireless transmitter/receivers 250. The user outputs 270 may include elements such as a display screen, speaker, vibration device, LED or other lights, and/or other output devices known in the art. In some embodiments, one or more of the user inputs 260 may be combined with one or more of the user outputs 270, as may be the case with a touch screen.

The desktop computer 122 may include various other components not shown or described herein. Those of skill in the art will recognize, with the aid of the present disclosure, that any such components may be used to carry out the methods set forth herein, in addition to or in the alternative to the components shown and described in connection with FIG. 2A.

The desktop computer 122 may be capable of carrying out the methods of the present disclosure in a standalone computing environment, i.e., without relying on communication with other devices such as the other computing devices 120 or the servers 150. In other embodiments, the methods presented herein may be utilized in different computing environments. One example of a client/server environment will be shown and described in connection with FIG. 2B.

Figure 2B:
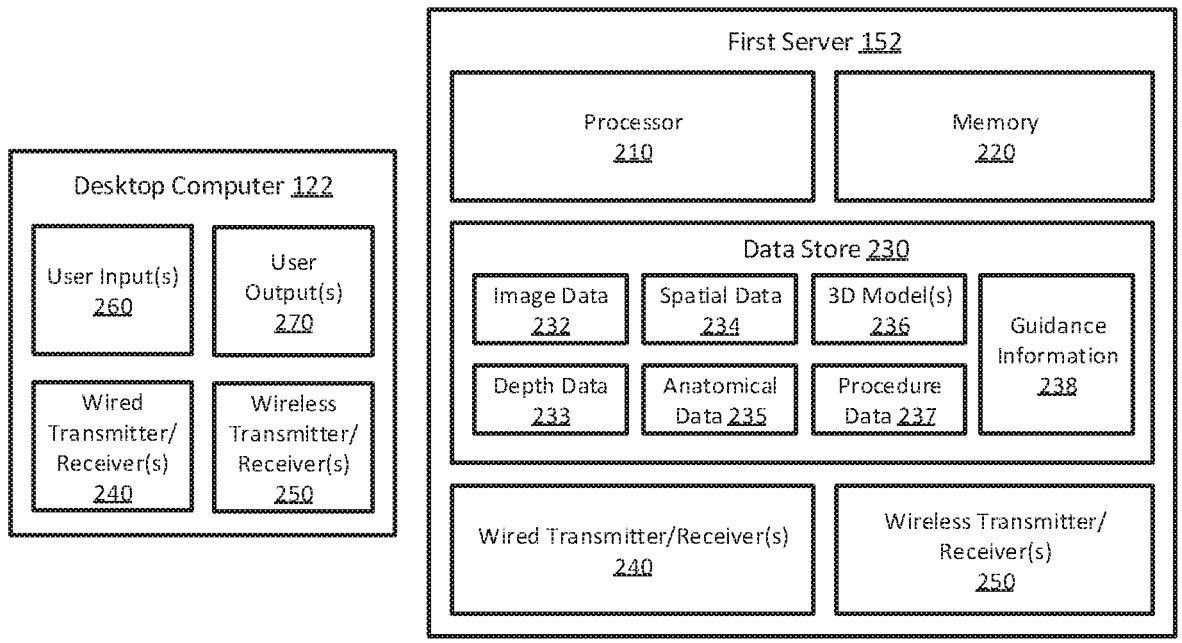
FIG. 2B is a schematic block diagram illustrating the desktop computer of FIG. 1, and a server in the form of the first server of FIG. 1, which may cooperate to enable practice of the disclosure with client/server architecture, according to one embodiment of the disclosure.

Referring to FIG. 2B, a schematic block diagram illustrates a computing device in the form of the desktop computer 122 of FIG. 1, and a server in the form of the first server 152 of FIG. 1, which may cooperate to enable practice of the methods set forth herein with client/server architecture. As shown, the desktop computer 122 may be a "dumb terminal," made to function in conjunction with the first server 152.

Thus, the desktop computer 122 may have only the hardware needed to interface with a user (such as the first user 112 of FIG. 1) and communicate with the first server 152. Thus, the desktop computer 122 may include one or more user inputs 260, one or more user outputs 270, one or more wired transmitter/receivers 240, and/or one or more wireless transmitter/receivers 250. These components may be as described in connection with FIG. 2A.

Computing functions (apart from those incident to receiving input from the user and delivering output to the user) may be carried out in the first server 152. Thus, the processor 210, memory 220, data store 230, wired transmitter/receivers 240, and wireless transmitter/receivers 250 may be housed in the first server 152. These components may also be as described in connection with FIG. 2A.

In operation, the desktop computer 122 may receive input from the user via the user inputs 260. The user input may be delivered to the first server 152 via the wired transmitter/receivers 240 and/or wireless transmitter/receivers 250. This user input may be further conveyed by any intervening devices, such as the first router 132 and any other devices in the local area network 142 that are needed to convey the user input from the first router 132 to the first server 152.

The first server 152 may conduct any processing steps needed in response to receipt of the user input. Then, the first server 152 may transmit user output to the user via the wired transmitter/receivers 240, and/or wireless transmitter/receivers 250. This user output may be further conveyed by any intervening devices, such as the first router 132 and any other devices in the local area network 142 that are needed to convey the user output from the first server 152 to the first router 132. The user output may then be provided to the user via the user outputs 270.

Figure 3:
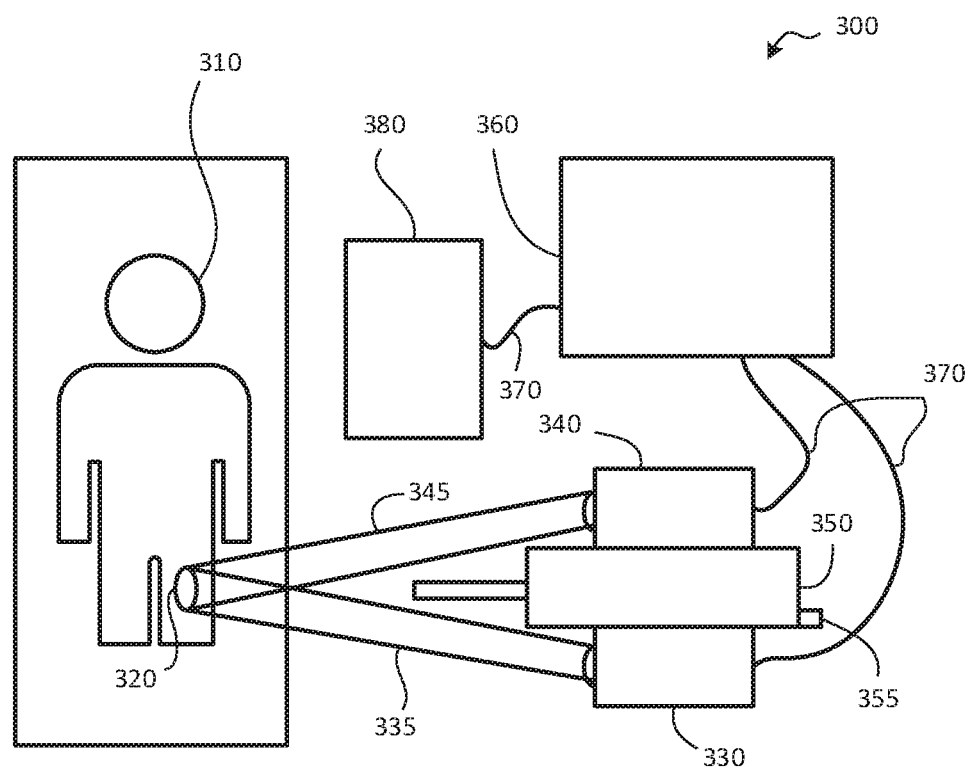
FIG. 3 depicts a surgical guidance system, according to one embodiment of the disclosure.
Figure 4:
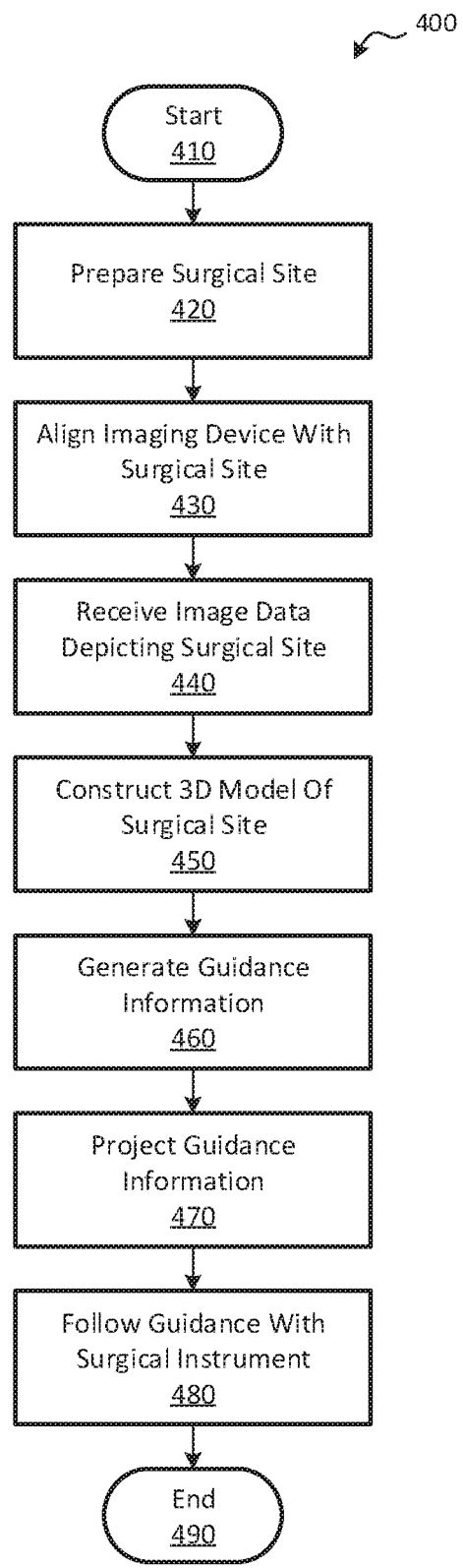
FIG. 4 is a flowchart diagram illustrating a method for carrying out a surgical procedure, according to one embodiment of the disclosure.
Figure 5:
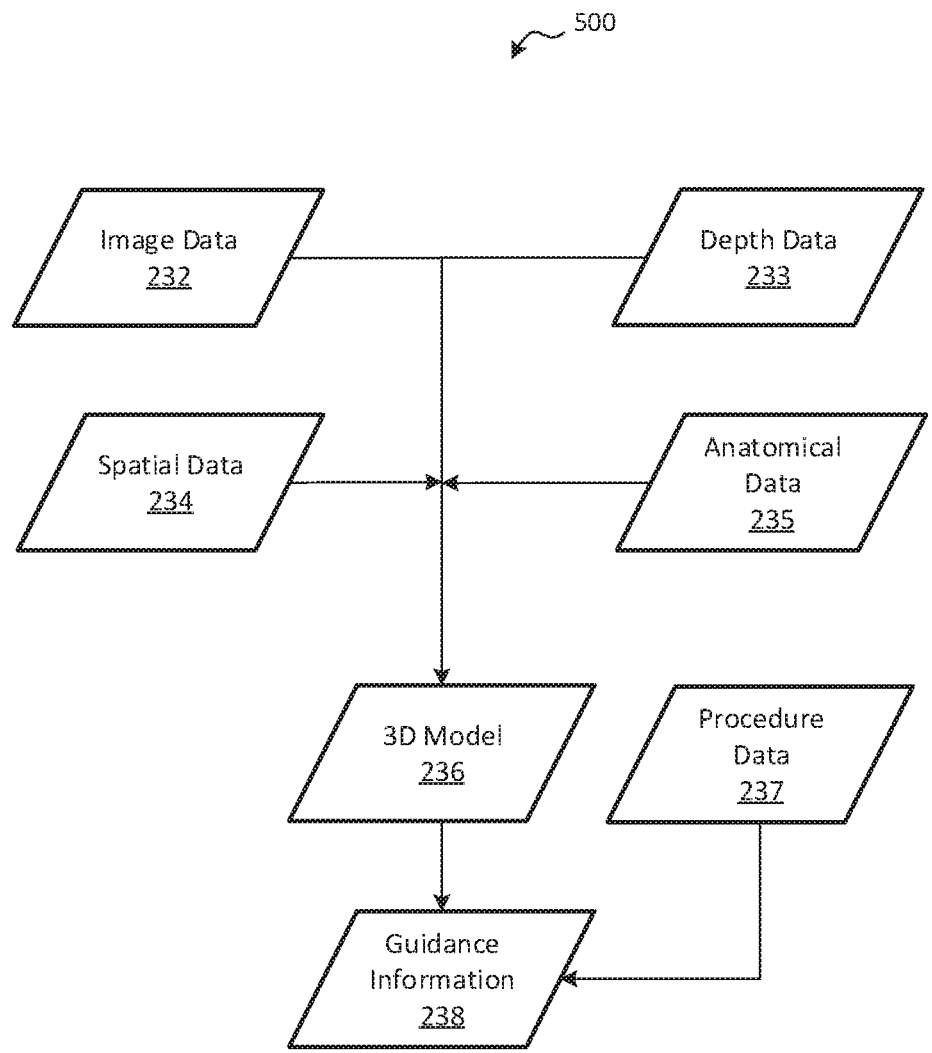
FIG. 5 is a schematic block diagram depicting data flow, according to one embodiment of the disclosure.
Figure 6:
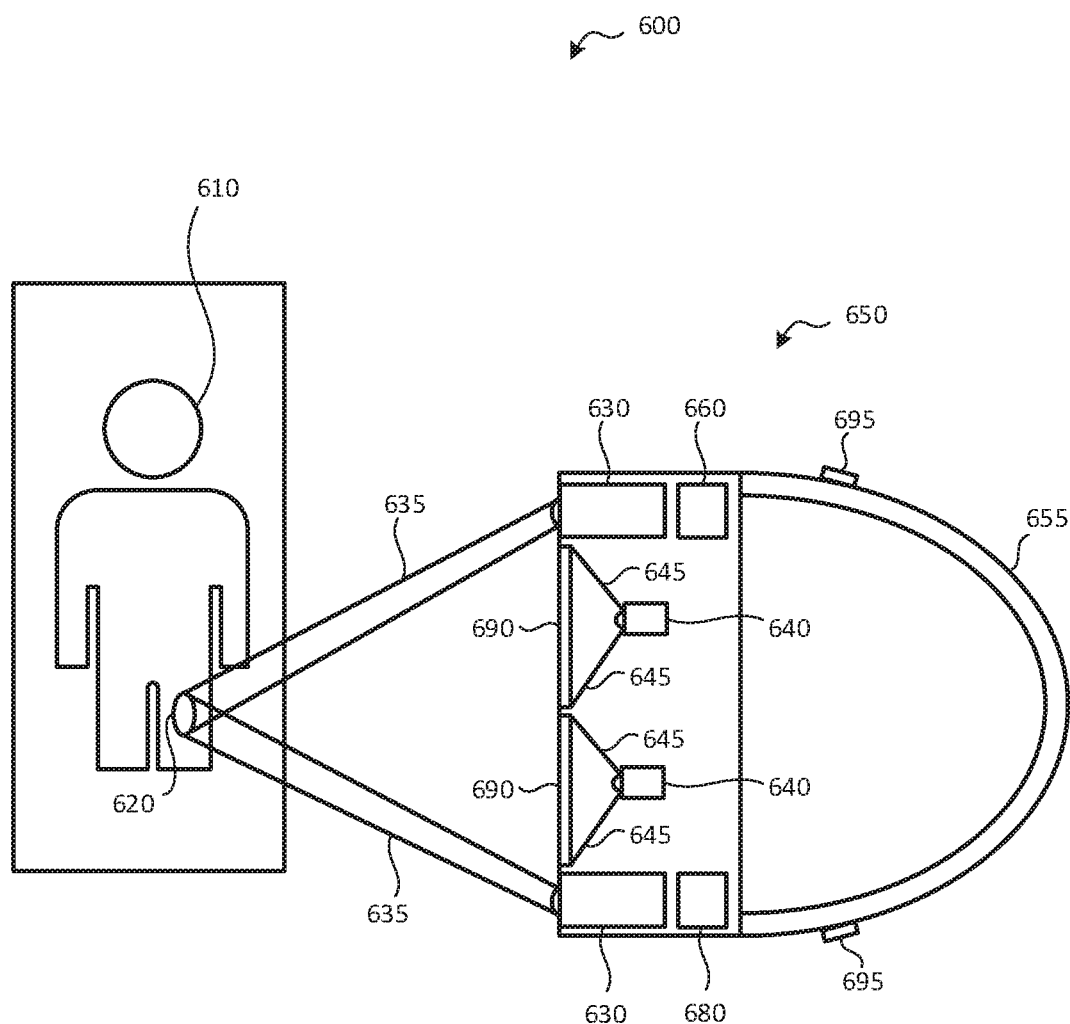
FIG. 6 depicts a system for guiding a surgical procedure based on a surgical procedure plan, according to one embodiment of the disclosure.

FIGS. 3-9 illustrate various systems and methods relating to surgical guidance techniques, as will be explained in more detail below with reference to each of these individual Figures. For example, FIGS. 3 and 6 illustrate alternative examples of systems for guiding a surgical procedure based on a surgical procedure plan. In general, each of these alternative systems may include an image capture device that captures one or more images of an exposed anatomical feature of a patient at a surgical site. Each of these systems may also include a computing device configured to receive a surgical procedure plan. The surgical procedure plan may be based on one or more desired attributes related to an anatomical 3D model that represents the exposed anatomical feature of the patient at the surgical site. The computing device may also be configured to register the anatomical 3D model to the exposed anatomical feature of the patient based on images of the exposed anatomical feature. In addition, each of these alternative systems may also include a projector that provides guidance information to the surgeon based on the surgical procedure plan. In this manner, each of these alternative systems may facilitate performance of the surgical procedure at the surgical site by the surgeon.

Referring now to FIG. 3, a schematic block diagram depicts a surgical guidance system, or system 300, according to one embodiment. The system 300 may be used to assist in any of a wide variety of surgical procedures. In the non-limiting exemplary illustration of FIG. 3, the system 300 may be used to facilitate the performance of a knee replacement surgery on a patient 310 at a surgical site 320 proximate the knee of the patient 310. The system 300 may include an image capture device 330, a projector 340, a surgical instrument 350, a computing device 360, and/or other sensors 380.

As shown in the example of FIG. 3, the image capture device 330 and/or the projector 340 may be coupled to the surgical instrument 350. However, it will be understood that in other embodiments the image capture device 330 and/or the projector 340 may not be coupled to the surgical instrument 350. The image capture device 330 may capture one or more images of an exposed anatomical feature of the patient at the surgical site 320. In this example, the exposed anatomical feature of the patient may include an exposed portion of a bone of the patient, such as an exposed portion of a tibial bone, a femoral bone, and/or a patellar bone of the patient. The computing device 360 may receive a surgical procedure plan that may be patient-specific. For example, the surgical procedure plan may be based on one or more desired attributes related to an anatomical 3D model 236 representing the exposed anatomical feature of the patient at the surgical site 320, such as an exposed portion of a tibial bone, a femoral bone, and/or a patellar bone of the patient. The computing device 360 may then register the anatomical 3D model 236 to the exposed anatomical feature of the patient based on one or more images of the exposed anatomical feature taken by the image capture device 330. In this manner, the morphology of the anatomical 3D model 236 of the patient's bone(s) may be matched up with the actual morphology of the patient's bone(s) exposed at the surgical site 320 during the knee replacement surgery. Once this registration process is complete, the computing device 360 may then access and utilize data relating to the surgical procedure plan in order to guide the surgeon through the surgical procedure. This may be accomplished with the projector 340, which may project light onto the exposed anatomical feature of the patient at the surgical site 320 to guide the surgeon through the surgical procedure. For example, the projector 340 may project light 345 onto an exposed bone of the patient to indicate to the surgeon where to drill a hole in the exposed bone and/or indicate to the surgeon which portion(s) of the bone should be resected, etc.

In a particular example, the surgical procedure plan may include data that identifies desired locations and/or orientations for at least two parallel pin holes (not shown) to be formed in the exposed portion of the bone based on the anatomical 3D model 236 in the surgical procedure plan. The at least two parallel pin holes may be sized, oriented, spaced apart, and configured to receive at least two pins (not shown) which may then be used to secure a cutting guide (not shown) to the exposed portion of the bone. Once this cutting guide is properly aligned and secured to the bone, corresponding bone resections may then be made based on the specific shape and characteristics of the cutting guide. In this example, the projector 340 may be configured to project light 345 onto the exposed portion of the bone to indicate the desired locations and/or orientations for the at least two parallel pin holes to be formed in the exposed portion of the bone based on the surgical procedure plan. In a particular example, the projector 340 may be configured to project laser light 345 onto the exposed portion of the bone to indicate desired locations and/or orientations for surgical operations. The system 300 may continuously calculate the relative position of the surgical instrument 350 relative to the exposed portion of the bone and continuously modify the angle of projection of the laser light 345 from the projector 340 to ensure that the laser light 345 projects to the proper position on the exposed portion of the bone and indicate the desired locations and/or orientations for surgical operations, such as drilling holes, performing resections, etc. The projector 340 may utilize a wide variety of laser projection technologies, including but not limited to: a standard-LED laser, a laser-scanning pico-projector system, a mirror-directed laser system, etc.

In another particular example, the surgical instrument 350 may be a drill tool with an audio device 355 coupled to the drill tool. The audio device 355 may be configured to produce a sound that indicates whether the drill tool is properly aligned with the desired locations and/or axial orientations of the at least two parallel pin holes to be formed in the exposed portion of the bone based on the surgical procedure plan. For example, the audio device 355 may emit a sound, such as a constant tone or frequency (as one non-limiting example), when the drill tool is properly aligned with a desired location and/or axial orientation for a pin hole that is to be formed in the bone in accordance with the surgical procedure plan.

The image capture device 330, as well as other image capture devices disclosed herein, may include any of a wide variety of image capture devices that receive electromagnetic energy 335 and generate corresponding images. The electromagnetic energy 335 from which the images are generated may include frequencies within and/or outside of the visible spectrum.

In some embodiments, the image capture device 330 may include a light detection and ranging ("LiDAR") system that generates point cloud data through the use of a rotatable pulsing laser rangefinder. The point cloud data may be considered an "image," and may be used as a depth map indicative of the depth of points on an object surface from the LiDAR sensor. Thus, the output from the LiDAR sensor may be a form of the image data 232 and/or the depth data 233 described earlier. Each of the LiDAR imaging techniques disclosed herein, and explained above in more detail, may further utilize any appropriate scaling techniques, optics, lenses, etc., which may be necessary to achieve a desired precision that is suitable for a given surgical procedure. For example, a LiDAR imaging technique utilized to create a 3D image of an exposed bone of a patient may incorporate any appropriate scaling techniques, optics, lenses, etc., which may be necessary in order to achieve a desired precision that is suitable to allow proper registration of the 3D image of the exposed bone of the patient with a 3D anatomical model 236 of the bone of the patient which may have been created prior to the surgical procedure, as will be explained in more detail below.

Additionally or alternatively, the image capture device 330 may include a camera of a type that detects visible light, thereby providing a form of the image data 232 described earlier. Such images may be processed in ways that enable determination of the 3D geometry of objects appearing in the images, particularly where multiple image capture devices 330 are used from positions offset from each other. The resulting images may be compared to ascertain depth, and thence geometry, in the generation of the 3D models 236. In some embodiments, the image capture device 330 may be a light-field camera such as a plenoptic light-field camera with a microlens array, or a tiled camera array.

The image capture device 330 may be stationary or mobile. For example, the image capture device 330 may be mounted on the surgical instrument 350 as depicted in FIG. 3, and may thus move with the surgical instrument 350 relative to the surgical site 320. In the alternative to mounting the image capture device 330 on the surgical instrument 350, the image capture device 330 may be designed to move along a predictable pathway, as the image capture device 330 may be secured to an arm or other device that translates and/or rotates relative to the surgical site 320. Alternatively, the image capture device 330 may be located in a remote stationary position relative to the surgical site 320.

In some embodiments, more than one image capture device 330 may be used. It may be beneficial to displace multiple image capture devices 330 apart from each other to enhance the accuracy of 3D models 236 generated from the images. If desired, multiple different types of imaging devices may be used. For example, image capture devices 330 may include, but are not limited to: visual light cameras, photographic video cameras, light-field cameras, plenoptic light-field cameras, 3D cameras, depth sensing cameras, environment mapping cameras, LiDAR sensors, time of flight sensors, infrared cameras, X-ray imaging devices, and/or any combination thereof.

In addition to, or in the alternative to the foregoing, various technologies may be incorporated into and/or used in conjunction with the image capture device 330 to facilitate generation of the 3D models 236. These may include, but are not limited to: (1) Digital Image Correlation; (2) Structured Illumination; (3) 3D Cameras; (4) Time-of-Flight Sensors; (5) Modulated light LiDAR systems; (6) Polarized Light Imaging; and (7) Quality Control Systems. Each of these technologies will be briefly described below in more detail.

(1) Digital Image Correlation: Digital image correlation may optically measure deformation on the surface of an object. Changes in the gray value pattern may be tracked within small regions of an image, called "subsets," during deformation. This may be done, for example, by capturing images of the surface before and after deformation. In the course of this process, 3D models may be generated, with optional display of stresses and strains. Such methods may be used, for example, to image and model body parts before and after performance of a surgical procedure to assess geometric changes and/or determine stresses. More detail regarding digital image correlation may be found at:

http://correlatedsolutions.com/digital-image-correlation/.

(2) Structured Illumination: Structured illumination projects a pattern of illumination on an object, such as a series of lines, bars, dots, and/or the like. The pattern may be a one-dimensional pattern (such as a series of spaced apart lines), or a two-dimensional pattern (such as a grid or other pattern in which elements are displaced from each other in two orthogonal dimensions). Contouring, positions, and/or orientations of the patterned elements may be measured to ascertain the shape of the underlying surfaces on which the pattern is projected. The illumination may utilize visible light and/or invisible electromagnetic energy. This system is used by the Microsoft Kinect™ system to read the 3D positions and/or orientations of players of video games. More detail regarding structured illumination can be found at:

http://www.3dunderworld.org/an-open-source-structured-light-scanning-system-for-rapid-geometry-acquisition/, and at:

https://en.wikipedia.org/wiki/Kinect.

(3) 3D Cameras: 3D cameras may be designed to capture multiple images of a scene. The shapes, positions, and/or orientations of objects in the scene may then be obtained by comparing the images. As mentioned previously, this may be accomplished through the use of plenoptic light-field cameras or camera arrays. Additionally or alternatively, a simple stereotactic camera may be used, as described at:

https://www.lhup.edu/~dsimanek/3d/stereo/ 3dgallery23.htm.

Triangulation may also be used to ascertain 3D geometry, as set forth at:

https://en.wikipedia.org/wiki/Triangulation %28computer vision%29.

(4) Time-of-Flight Sensors: A time-of-flight sensor may illuminate a scene with a modulated light source (emitting visual and/or invisible light), and may observe the reflected light. The phase shift between illumination and reflection may be measured and used to ascertain the distance the light has travelled, thereby enabling the generation of a depth map indicative of the depth of objects in the scene from the camera. 3D models can be built from depth maps. More detail regarding time-of-flight sensors can be obtained at:

http://www.ti.com/lit/wp/sloa190b/sloa190b.pdf (for pulsed light).

(5) Modulated light LiDAR systems: A modulated light LiDAR system may use modulated light in conjunction with LiDAR sensing. Modulation can be used to enhance the operation of the LiDAR. In some examples, the LiDAR sensor may read the modulation of the light received to ascertain the angle from which the light was emitted, the time at which the light was emitted, and/or other information that enables the enhancement of the resulting depth information, thereby helping to generate more accurate 3D models. More detail regarding modulated light LiDAR systems can be obtained at:

http://encyclopedia2.thefreedictionary.com/Modulation+ of+Light.

(6) Polarized Light Imaging: Polarized light imaging may use the scattering of light by tissue structures such as cell nuclei, mitochondria, membranes, and the like to determine the contrast level of the image. Multiple images may be used with different types of polarized light and/or light polarized along different directions to provide a more complete picture of the tissue structures. Simple polarized imaging may be used to survey superficial structures to find the margins of various pathologies. More detail regarding polarized light imaging can be obtained at:

http://www.lumamed.com/documents/5 polarized%20light%20imaging.pdf, and at:

http://omlc.org/~prahl/pubs/pdf/ramella03b.pdf.

(7) Quality Control Systems: Various quality control systems may use any combination of imaging technologies, including but not limited to those imaging technologies set forth above. Some such systems may use augmented reality, or virtual reality, in the form of projection to indicate the presence of defects or the like. Any such technologies may be incorporated into the image capture device 330 and/or the projector 340. One exemplary system that may be incorporated into the image capture device 330 and/or the projector is described at:

http://8-tree.com/technology/.

Some of the systems and methods set forth above may use active illumination. Accordingly, one or more active electromagnetic energy sources may be used to illuminate the surgical site 320 with electromagnetic energy with the appropriate frequency (for example, visible light, infrared light, ultraviolet light, radio waves, X-rays, gamma rays, etc.) to reflect electromagnetic energy 335 to the image capture device 330. Multiple image capture devices 330 may include any combination of stationary and/or movable sensors.

FIG. 3 depicts usage of the image capture device 330 to gather electromagnetic energy 335 after exposure of the surgical site 320. However, the image capture device 330 may be applied at any stage of the surgical procedure. For example, the image capture device 330 may be used prior to commencement of the surgical procedure to visualize tissues surrounding the surgical site 320 that are to be penetrated and/or retracted to provide access. The image capture device 330 may be used during provision of access to the surgical site 320 to help direct the incisions being made. After exposure of the surgical site 320, the image capture device 330 may be used to guide resection and/or other preparatory steps, implant placement, and/or placement of ligaments and/or other tissues after the implants have been placed.

Notably, various types of data may also be gathered at different times. For example, in some embodiments, the anatomical data 235 may be gathered pre-operatively, via CT scans, X-ray imaging, MRI imaging, MRT imaging, fluoroscopy, and the like. Then, the image data 232, the depth data 233, and/or the spatial data 234 may be gathered during performance of the surgical procedure.

The image capture device 330 may generate the image data 232, the depth data 233, the spatial data 234, and/or the anatomical data 235. If desired, one or more of these data types may be obtained through the use of other sensors 380, which may be optional. Such other sensors 380 may include, for example, position and/or orientation sensors that, rather than generating images, detect the locations and/or orientations of objects within the environment to provide the spatial data 234. For example, passive and/or active illuminators, such as RFID tags, reflectors, fiducial markers, or the like, may be attached to objects that are to be tracked or measured. The other sensors 380 may also include, but not limited to: a photographic video camera, a 3D camera, a depth sensing camera, an environment mapping camera, an infrared camera, a light-field camera, a plenoptic light-field camera, a time of flight sensor, a LiDAR sensor, an ambient light sensor, a proximity sensor, an eye-tracking sensor, a head-tracking sensor, an accelerometer, a gyroscope, a magnetometer, and the like.

The projector 340 may be any device that can present data, such as the guidance information 238, to a viewer, such as a surgeon, while preserving the ability of the viewer to also view the surgical site 320. Thus, the projector 340 may be designed to present the guidance information 238 to the viewer in the form of light projected onto the patient or in the form of an augmented reality experience, as will be discussed in more detail below. Thus, the projector 340 may, for example, project the guidance information 238 onto the surgical site 320 itself, or onto a screen interposed between the viewer and the surgical site 320, such as a set of partially reflective, yet translucent lenses worn by the viewer, as will be discussed in more detail below with reference to FIG. 6.

For the example of knee replacement surgery, the projector 340 may beneficially project the guidance information 238 directly onto the surfaces of one or more tissues or bones, such as a tibia, a femur, and/or a patella, involved in the surgery. The exposed surface of a bone may make an adequate screen for reflecting projected visual light 345 back toward a viewer. In orthopedic surgery, it may be particularly helpful to project the locations of cuts or holes to be made in the bone. This may be of particular help when the surgical instrument 350 is the instrument used to make such cuts, such as a bone saw, reamer, drill, etc.

Various types of projection technologies may be incorporated into the projector 340. For example, the projector 340 may include LED, DLP, LCD, lasers, waveguides, diffraction grating, combiners, liquid crystal on silicon (LQoD), total internal reflection (TIR), or other projection technologies. The projector 340 may project in color and/or in black and white, and may project still and/or moving imagery which may be continuously updated in real-time based on one or more captured images. The projector 340 may be stationary, or may move. In the exemplary embodiment of FIG. 3, the projector 340 is shown mounted to the surgical instrument 350. However, in alternative embodiments, the projector 340 may be mounted on a different movable apparatus, such as lenses that are worn by the viewer, a translating and/or rotating arm, or the apparatus may also be stationary. Multiple projectors 340 may also be used as desired. Multiple or moving projectors 340 may be particularly useful where the surgical site 320 is to be moved during surgery, as is needed for some surgical procedures.

Like the image capture device 330, the projector 340 may be used at various stages of the surgical procedure. The projector 340 may be used to project guidance information 238 that helps locate an access point to access the surgical site 320, facilitate the process of accessing the anatomy after completion of the main phase of the surgical procedure. Thus, the projector 340 may be used to project the guidance information 238 onto soft tissue such as skin, onto hard tissue such as bone, or even onto non-anatomical elements such as other instruments involved in the surgical procedure.

Notably, the projector 340 need not be used at the same stage of the surgical procedure as the image capture device 330. For example, the image capture device 330 may be used prior to accessing the surgical site 320, particularly where the image capture device 330 includes an X-ray detector, fluoroscopy device, or other sensor capable of penetrating soft tissues. The 3D models 236 may also be made based on the images received by the image capture device 330, and then subsequently used to project the guidance information 238 onto the surgical site 320.

The surgical instrument 350 may be any type of surgical instrument. Some examples include, but are not limited to: tissue dilators, retractors, measuring devices, cutting devices, inserters, distractors, persuaders, fastener drivers, and the like. Where the surgical instrument 350 is a cutting instrument, it may be of particular use for the projector 340 to project the guidance information 238 in the form of one or more cutting locations on the hard or soft tissues to be cut.

As indicated previously, mounting of the image capture device 330 and the projector 340 on the surgical instrument 350 is optional. Such mounting may provide some unique benefits in terms of the surgeon's ability to naturally aim the image capture device 330 and/or the projector 340 at the surgical site 320 while directing the surgical instrument 350 at the surgical site 320.

The computing device 360 may be any type of computing device, including but not limited to the desktop computer 122, the laptop computer 124, the smartphone 126, and the camera 128 mentioned above, or any other suitable computing device. The computing device 360 may be coupled to the image capture device 330, the projector 340, and/or the other sensors 380 via wires 370, or alternatively, via wireless connections.

The computing device 360 may receive images and/or other sensor data from the image capture device 330 and/or the other sensors 380, and may thus receive the image data 232, the depth data 233, the spatial data 234, and/or the anatomical data 235. The computing device 360 may use any of these data types, as applicable, to generate the 3D models 236. Then, the computing device 360 may apply the procedure data 237 to the 3D models 236 to generate the guidance information 238.

The computing device 360 may provide the guidance information 238 to the projector 340. If desired, the guidance information 238 may be provided by the computing device 360 in the form of one or more two-dimensional images that can easily be projected by the projector 340 onto the desired surface. The guidance information 238 may be static, or may change over time. In some examples, the computing device 360 may operate in a continuous cycle, receiving data from the image capture device 330 and/or the other sensors 380, and generating updated guidance information 238 to be projected for viewing by the viewer. The guidance information 238 may thus be updated based on steps taken by a surgeon to modify the surgical site 320.

For example, for implantation of a knee implant, the guidance information 238 may first indicate the cuts to be made to a femur or tibia to resect away natural articular surfaces, and then after the resection is complete, the guidance information 238 may instead indicate holes to be reamed to anchor the implant to the resected bony surface. If desired, after resection, the image capture device 330 and/or the other sensors 380 may operate to capture additional data that enables the generation of the 3D models 236 inclusive of the bone in the resected state. Then, the computing device 360 may generate the guidance information 238 indicating the holes to be reamed based on the actual cuts made by the surgeon to resect the bone, rather than the cuts that were previously indicated in the guidance information 238. Thus, differences between the guidance information 238 for a step, and the procedure followed by the surgeon to carry out that particular step, may be accounted for in the projection of guidance information 238 for future steps.

FIG. 4 is a flowchart diagram of a method 400 for carrying out a surgical procedure, according to one embodiment. The method 400 will be described in connection with the system 300 of FIG. 3. However, those of skill in the art will recognize that alternative systems may be used in the performance of the method 400, and the system 300 may be utilized in connection with alternative methods.

The method 400 may start 410 with a step 420 in which the surgical site 320 is prepared. Depending on the stage of the surgical procedure in which the system 300 is to be used, this may simply entail cleaning the surgical site 320 for projection of the guidance information 238 directly on the skin. Alternatively, the step 420 may entail accessing the surgical site 320, either partially or completely.

In a step 430, the image capture device 330 may be aligned with the surgical site 320. The image capture device 330 may have a field-of-view. Performance of the step 430 may entail positioning the surgical site 320 within the field-of-view. The image capture device 330 may have a wide field of view, causing the step 430 to be successfully completed without the need to precisely orient the image capture device 330 relative to the surgical site 320. In the alternative, the image capture device 330 may have a narrower field-of-view, requiring more precise orientation of the image capture device 330 relative to the surgical site 320. Where the image capture device 330 is mounted to the surgical instrument 350, as in FIG. 3, the step 430 may be carried out by orienting the surgical instrument 350 relative to the surgical site 320, for example, by hand.

In a step 440, image data 232 depicting the surgical site 320 may be received from the image capture device 330 and/or the other sensors 380. Additionally or alternatively, depth data 233, spatial data 234, and/or anatomical data 235 may be received. Such data may be received in the computing device 360.

In a step 450, the 3D models 236 of the surgical site 320 may be constructed. The 3D models 236 may include one or more anatomical features, which may include hard and/or soft tissues. The 3D models 236 may be constructed with any necessary level of accuracy. In some embodiments, only portions of objects may be represented in the 3D models 236. For example, for knee replacement surgery, only the distal end of the femur and/or the proximal end of the tibia may be represented in the 3D models 236. Performance of the step 450 may include using any of a wide variety of known techniques to generate 3D geometry based on the image data 232, the depth data 233, the spatial data 234, and/or the anatomical data 235.

In a step 460, the guidance information 238 may be generated. This may be done by applying the procedure data 237 to the 3D models 236, as indicated previously. The procedure data 237 may provide particular actions to be taken relative to particular anatomical features. Such actions may be mapped out for the anatomy of the patient 310 through the use of the 3D models 236.

In a step 470, the guidance information 238 may be projected through the use of the projector 340. As mentioned previously, the guidance information 238 may be projected on any surface suitable for reflecting visible light back to the viewer, which will appear near the surgical site 320 from the viewpoint of the viewer. For example, the guidance information 238 may be projected on a hard tissue surface such as an exposed bone surface, on a soft tissue surface such as the skin of the patient 310, on the surgical instrument 350, on another instrument (not shown) used in the course of the surgical procedure, and/or on a screen interposed between the viewer and the surgical site 320.

In a step 480, the viewer, who may be a surgeon, may follow the guidance information 238 with the surgical instrument 350. The step 480 may include any of a number of surgical steps, including but not limited to moving tissue to access the surgical site 320, cutting tissue, attaching tissue, placing an implant, and the like. The surgeon may then complete the surgical procedure, and the method 400 may end 490.

The various steps of the method 400, or any other method disclosed herein, may be reordered, omitted, and/or replaced with different steps within the scope of the present disclosure. Those of skill in the art, with the aid of the present disclosure, will recognize that many variations may be made to the method 400, or any other method disclosed herein, depending on the particular surgical procedure to be carried out, as well as the configuration of the system used in the performance of that surgical procedure.

Various user controls may be present, and may enable the surgeon or other operator to control the operation of the system 300. For example, the image capture device 330, the projector 340, the surgical instrument 350, and/or the computing device 360 may each have user inputs that can be activated by the user to control imaging, computation, projection, and/or performance of a surgical operation on the patient 310. In some embodiments, such user inputs may be voice-activated.

In one embodiment, the user inputs on the surgical instrument 350 may be hand-operated so that the surgeon controls the surgical instrument 350 by hand, but the image capture device 330, the projector 340, and/or the computing device 360 may interact with a microphone through which voice commands are received to initiate imaging of the surgical site 320, initiate generation of the 3D models 236, and/or initiate or cease projection of the guidance information 238 at the surgical site 320. Simple voice commands such as "capture," "generate model," and "project" may be used, as well as any other suitable voice command.

FIG. 5 is a block diagram 500 depicting data flow, according to one embodiment. As shown, any of the image data 232, the depth data 233, the spatial data 234, and/or the anatomical data 235 may be obtained (as in the step 440 of FIG. 4, as one example) and used (as in the step 450 of FIG. 4, as one example) to generate the 3D models 236. The procedure data 237 for the surgical procedure to be performed may be retrieved and applied to the 3D models 236 to yield the guidance information 238 (as in the step 460 of FIG. 4, as one example). The guidance information 238 may then be projected (as in the step 470 of FIG. 4, as one example) and used to facilitate completion of the surgical procedure (as in the step 480 of FIG. 4, as one example).

FIG. 6 depicts a system 600 for guiding a surgical procedure based on a surgical procedure plan, according to another embodiment of the present disclosure. The system 600 may be used to assist in any of a wide variety of surgical procedures. In the non-limiting exemplary illustration of FIG. 6, the system 600 may be used to facilitate the performance of a knee replacement surgery on a patient 610 at a surgical site 620 proximate the knee of the patient 610. The system 600 may include a head-mounted display unit 650 which may be worn by a surgeon. The head-mounted display unit 650 may, or may not, be coupled to at least one image capture device 630, projector 640, translucent lenses 690, computing device 660, audio device(s) 695, other sensors 680, and/or head band 655.

The head-mounted display unit 650 may, in some embodiments, be a commercially-available augmented reality device, such as a HoloLens, available from Microsoft Corporation of Redmond, Wash. Such a head-mounted display unit may additionally or alternatively be used for pre-operative planning, as detailed elsewhere in this specification. In alternative embodiments, pre-operative planning may be carried out with any of a variety of commercially-available virtual reality devices, such as the Vive, available from HTC Corporation of New Taipei City, Taiwan, the Oculus Rift or the Oculus Go, available from Oculus VR, LLC of Menlo Park, Calif., or the Gear VR, available from Samsung Electronics of Seoul, South Korea.

The image capture device(s) 630 may be coupled to the head-mounted display unit 650 and may capture one or more images of an exposed anatomical feature of the patient at the surgical site 620. In this example, the exposed anatomical feature of the patient may include an exposed portion of a bone of the patient, such as an exposed portion of a tibial bone, a femoral bone, and/or a patellar bone. The computing device 660 may receive a surgical procedure plan that may be patient-specific. For example, the surgical procedure plan may be based on one or more desired attributes related to an anatomical 3D model 236 representing the exposed anatomical feature of the patient at the surgical site 620, such as the exposed portion of the tibial bone, femoral bone, and/or patellar bone of the patient.

The computing device 660 may be configured to register the anatomical 3D model 236 to the exposed anatomical feature of the patient based on one or more images of the exposed anatomical feature taken by the image capture device 630. In this manner, the morphology of the anatomical 3D model 236 of the patient's bone(s) may be matched up with the actual morphology of the patient's bone(s) that are exposed at the surgical site during the knee replacement surgery. Once this registration process is complete, the computing device 660 may access and utilize data relating to the surgical procedure plan in order to guide the surgeon through the surgical procedure. This may be accomplished with the projector(s) 640, which may be coupled to the head-mounted display unit 650.

The projector(s) 640 may be configured to project light 645 onto the translucent lenses 690, which may be at least partially reflected back into the eyes of the surgeon in order to display projected images within a surgeon's field-of-view in an overlaid, spaced relationship relative to the exposed anatomical feature of the patient at the surgical site 620. In this manner, the surgeon may simultaneously view the projected images overlaid on top of the actual exposed anatomical feature of the patient at the surgical site 620 in an augmented reality environment. The projected images may be 2D projections, 3D projections, holograms, partially translucent projections, opaque projections, simulated 3D projections, and the like. The projected images may include guidance information derived from the surgical procedure plan to help guide the surgeon through the surgical procedure. For example, the projector 640 may project images onto the translucent lenses 690 to indicate to the surgeon where to drill a hole in the exposed bone and/or to indicate to the surgeon which portion(s) of the bone should be resected, etc.

In a particular example, the surgical procedure plan may include data that identifies desired locations and/or orientations for at least two parallel pin holes (not shown) to be formed in the exposed portion of the bone based on the anatomical 3D model 236 of the surgical procedure plan. The at least two parallel pin holes may be sized, oriented, spaced apart, and configured to receive at least two pins (not shown) which may then be used to secure a cutting guide (not shown) to the exposed portion of the bone. Once this cutting guide is properly aligned and secured to the bone, corresponding bone resections may then be made based on the specific shape and characteristics of the cutting guide. In this example, the projector(s) 640 may be configured to project images onto the translucent lenses 690 to indicate the desired locations and orientations for the at least two parallel pin holes to be formed in the exposed portion of the bone, in accordance with the surgical procedure plan. Furthermore, the head-mounted display unit 650 may interact with a drill tool (not shown) to track the drill tool's location and orientation with respect to a patient's bone. The head-mounted display unit 650 may utilize the audio device(s) 695 coupled to the head-mounted display unit 650 to produce a sound that indicates whether the drill tool is properly aligned with the desired locations and/or axial orientations of the at least two parallel pin holes to be formed in the exposed portion of the bone, in accordance with the surgical procedure plan. For example, the audio device(s) 695 may emit sounds, such as a constant tone or frequency (as one non-limiting example), when the drill tool is properly aligned with a desired location and/or axial orientation for a pin hole that is to be formed in the bone in accordance with the surgical procedure plan.

Similar to previously described image capture device(s) discussed herein, the image capture device(s) 630 may include any of a wide variety of image capture devices that receive electromagnetic energy 635 and generate corresponding images. The electromagnetic energy 635 from which the images are generated may include frequencies within and/or outside of the visible spectrum.

In some embodiments, more than one image capture device 630 may be used. It may be beneficial to displace multiple image capture devices 630 apart from each other to enhance the accuracy of 3D models 236 generated from the images. If desired, multiple different types of imaging devices may be used. Example, image capture devices 630 may include, but are not limited to: visual light cameras, photographic video cameras, light-field cameras, plenoptic light-field cameras, 3D cameras, depth sensing cameras, environment mapping cameras, LiDAR sensors, time of flight sensors, infrared cameras, X-ray imaging devices, and/or any combination thereof.

The image capture device(s) 630 may generate the image data 232, the depth data 233, the spatial data 234, and/or the anatomical data 235. If desired, one or more of these data types may also be obtained through the use of other sensors 680, which may be optional. Such other sensors 680 may include, for example, position and/or orientation sensors that, rather than generating images, detect the locations and/or orientations of objects within the environment to provide the spatial data 234. For example, passive and/or active illuminators, such as RFID tags, reflectors, fiducial markers, or the like, may be attached to objects that are to be tracked or measured by the other sensors 680 and/or the image capture device(s) 630.

The other sensors 380 may also include, but not limited to: a photographic video camera, a 3D camera, a depth sensing camera, an environment mapping camera, an infrared camera, a light-field camera, a plenoptic light-field camera, a time of flight sensor, a LiDAR sensor, an ambient light sensor, a proximity sensor, an eye-tracking sensor, a head-tracking sensor, an accelerometer, a gyroscope, a magnetometer, and the like.

Various types of projection technologies may be incorporated into the projector(s) 640. For example, the projector(s) 640 may include LED, DLP, LCD, laser, waveguide, diffraction grating, combiner, liquid crystal on silicon (LQoD), total internal reflection (TIR), or other projection technologies. The projector(s) 640 may project in color and/or in black and white, and may project still and/or moving imagery.

Like the image capture device(s) 630, the projector(s) 640 may also be used at various stages of the surgical procedure. The projector(s) 640 may be used to project guidance information 238 that helps locate an access point to access the surgical site 620, facilitate the process of accessing the surgical site 620, carry out the surgical procedure, and/or assist in reconstruction of surrounding anatomy after completion of the main phase of the surgical procedure. Thus, the projector(s) 640 may be used to project the guidance information 238 in an overlaid fashion in augmented reality over soft tissue such as skin, over hard tissue such as bone, or even over non-anatomical elements such as other instruments involved in the surgical procedure.

Figure 7:
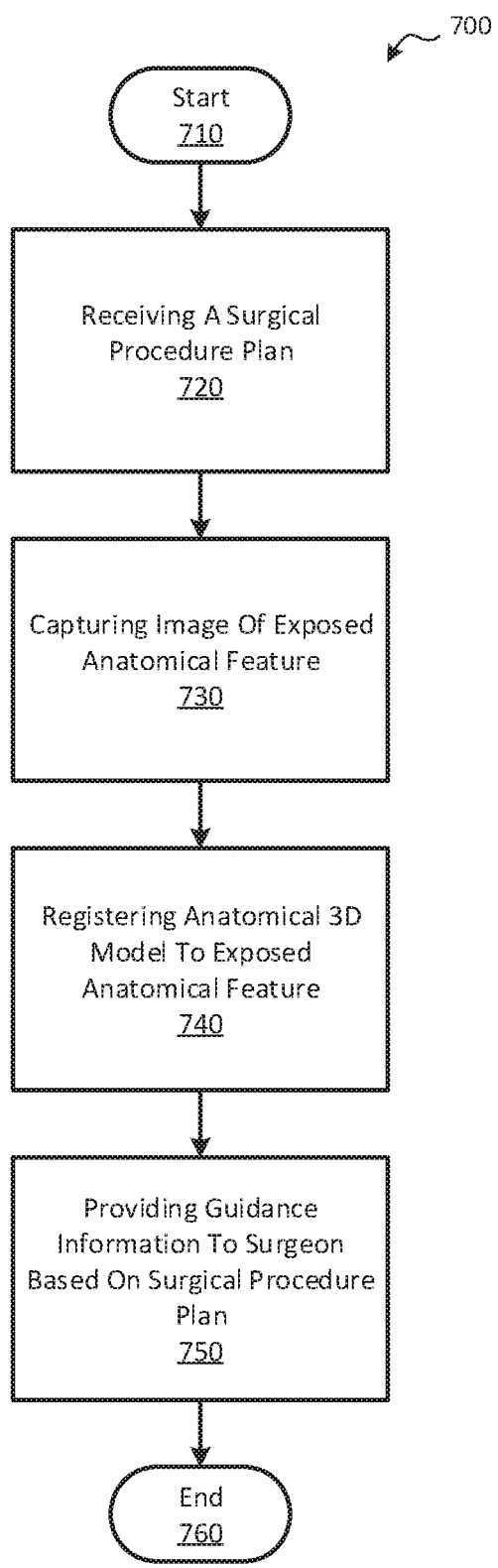
FIG. 7 is a flowchart diagram illustrating a method for guiding a surgical procedure based on a surgical procedure plan, according to one embodiment of the disclosure.

FIG. 7 is a flowchart diagram of a method 700 for guiding a surgical procedure based on a surgical procedure plan, according to embodiments of the present disclosure. The method 700 will be described in connection with the system 300 of FIG. 3 and the system 600 of FIG. 6. However, those of skill in the art will recognize that alternative systems may be used in the performance of the method 700, and the systems 300, 600 may be utilized in connection with other alternative methods.

The method 700 may start 710 with a step 720 in which a surgical procedure plan may be received. The surgical procedure plan may be based on one or more desired attributes related to an anatomical 3D model 236 that represents an anatomical feature of a patient at a surgical site. For example, the anatomical feature of the patient may include an exposed portion of a bone of the patient, such as an exposed portion of a tibial bone, a femoral bone, and/or a patellar bone of the patient, and the anatomical 3D model 236 may be representative of the exposed portion of the bone. The on one or more desired attributes related to the anatomical 3D model 236 may include, but are not limited to: an exact or approximate morphology map of a patient's bone; an exact or approximate morphology map of a patient's bone with a desired resection morphology; an exact or approximate morphology map of a patient's bone with one or more drill holes formed in the anatomical 3D model; Data relating to specific locations, orientations, spacing, and/or sizes of access points, incisions, drill holes, at least two parallel pin holes to be formed in the bone and configured to receive at least two pins to secure a cutting guide to the bone; Data relating to resection cuts to be made in a bone or other tissues; the specific implant(s) and/or instrument size(s) and/or type(s) to be used, and/or the locations, orientations, or sizes of the implants as they will appear after implantation is complete, etc.

In a step 730, at least one image of an exposed anatomical feature of the patient at the surgical site may be captured. This may be performed by at least one image capture device 330, 630 that is coupled to a surgical instrument 350, a head-mounted display unit 650, a stationary object, a movable object, and/or that is uncoupled from any object. Example image capture devices 330, 630 may include: visual light cameras, photographic video cameras, light-field cameras, plenoptic light-field cameras, 3D cameras, depth sensing cameras, environment mapping cameras, LiDAR sensors, time of flight sensors, infrared cameras, X-ray imaging devices, and/or any combination thereof.

In a step 740, the anatomical 3D model 236 may be registered to the exposed anatomical feature of the patient at the surgical site 320, 620 based on one or more images of the exposed anatomical feature. In this manner, the morphology of the anatomical 3D model 236 of the patient's anatomical feature may be matched up with the actual morphology of the patient's anatomical feature exposed at the surgical site 320, 620 during surgery.

In a step 750, guidance information 238 may be provided to a surgeon based on the surgical procedure plan to facilitate performance of the surgical procedure at the surgical site 320, 620 by the surgeon. This may be performed by at least one projector 340, 640 that is coupled to a surgical instrument 350, a head-mounted display unit 650, a stationary object, a movable object, and/or that is uncoupled from any object. Various types of projection technologies may be incorporated into the projector 340, 640. For example, the projector 340, 640 may include LED, DLP, LCD, laser, waveguide, diffraction grating, combiner, liquid crystal on silicon (LQoD), total internal reflection (TIR), and/or other projection technologies. The projector 340, 640 may project in color and/or in black and white, and may project still and/or moving imagery which may be continuously updated in real-time based on one or more captured images. The projector 340, 640 may be configured to project light onto the exposed anatomical feature of the patient at the surgical site 320, 620 to guide the surgeon through the surgical procedure. Alternatively, the projector 340, 640 may be configured to project images onto one or more translucent lenses 690 coupled to a head-mounted display unit 650 in order to display projected images within a surgeon's field-of-view in an overlaid spaced relationship relative to the exposed anatomical feature of the patient at the surgical site 320, 620 in order to guide the surgeon through the surgical procedure. In a particular example, the projector 340, 640 may be configured to project light onto an exposed portion of a bone to indicate desired locations and/or orientations for at least two parallel pin holes to be formed in the exposed portion of the bone. Alternatively, the projector 340, 640 may be configured to project images onto one or more translucent lenses 690 to indicate the desired locations and/or orientations for the at least two parallel pin holes to be formed in the exposed portion of the bone. In yet another particular example, guidance information 238 may be provided to the surgeon by emitting an audible sound to indicate when a surgical instrument 350, such as a drill tool, is properly aligned with a desired location and axial orientation of a pin hole that is to be formed in the bone, and/or when a cutting tool is properly aligned with the desired locations and orientations of resection cuts that are to be formed in the bone. In these examples, a constant tone or frequency (as one non-limiting example), may be used to indicate when the surgical instrument 350 is properly aligned with a desired location and/or orientation. The surgeon may then complete the surgical procedure, and the method 700 may end 760.

The various steps of the method 700, or any other method disclosed herein, may be reordered, omitted, and/or replaced with different steps within the scope of the present disclosure. Those of skill in the art, with the aid of the present disclosure, will recognize that many variations may be made to the method 700, or any other method disclosed herein, depending on the particular surgical procedure to be carried out, as well as the configuration of the system used in the performance of that surgical procedure.

Figure 8:
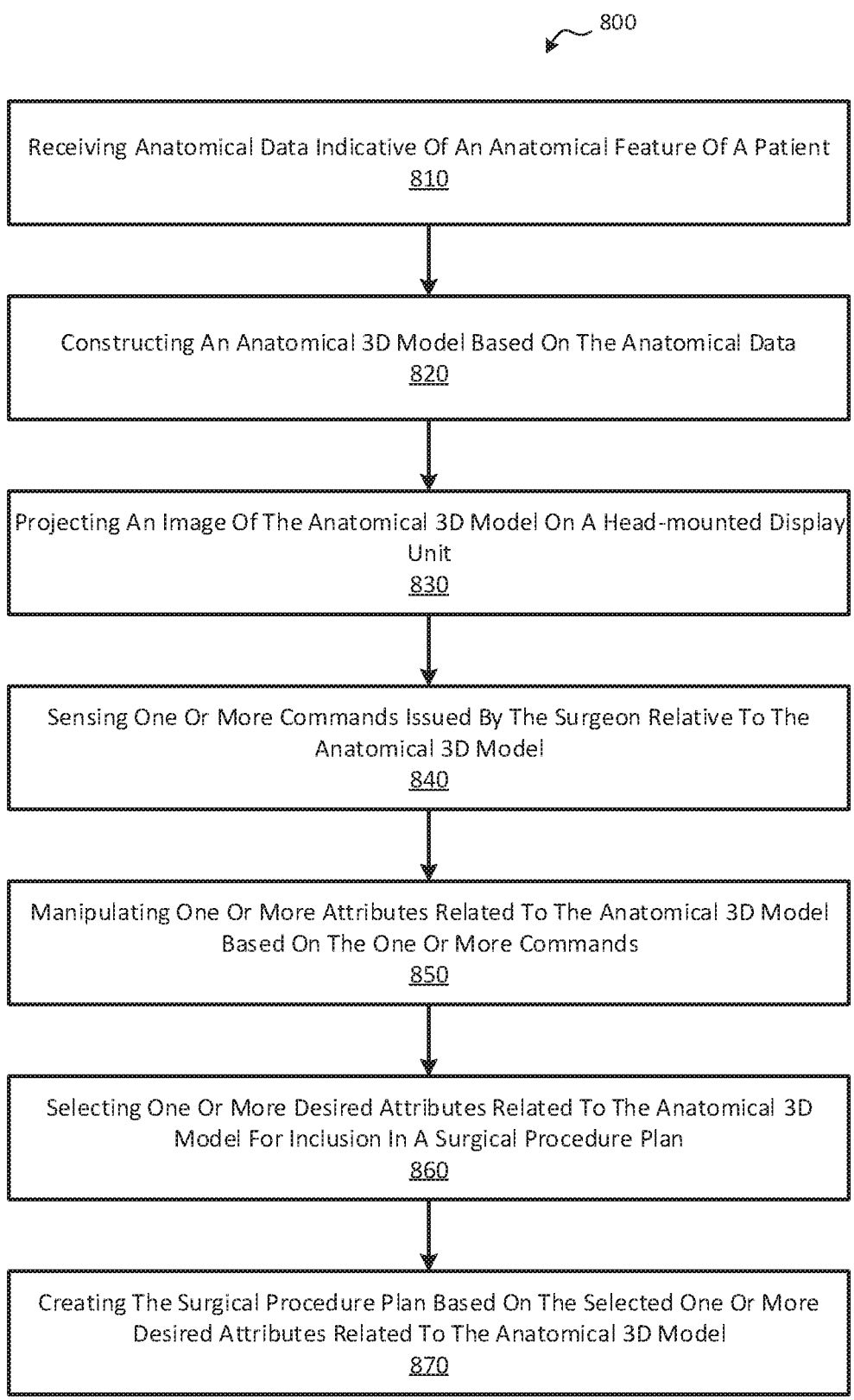
FIG. 8 is a flowchart diagram illustrating a method for creating a surgical procedure plan, according to one embodiment of the disclosure.

FIG. 8 is a flowchart diagram illustrating a method 800 for creating a surgical procedure plan. The method 800 will be described in connection with the head-mounted display unit 650 shown in FIG. 6. However, those of skill in the art will recognize that alternative systems may be used in the performance of the method 800, and the head-mounted display unit 650 may be utilized in connection with alternative methods. For example, although the head-mounted display unit 650 shown in FIG. 6 utilizes an augmented reality environment, due to the use of translucent lenses 690, other head-mounted display units that utilize virtual reality environments may also be used.

The method 800 may begin with a step 810 in which anatomical data 235 indicative of an anatomical feature of a patient at a surgical site 320, 620 may be received. The anatomical data 235 may include: CT scan data, MRT data, MRI data, 2D x-ray data, 3D x-ray data, and/or 2D x-ray data that has been converted to 3D x-ray data. The anatomical data 235 may relate to an anatomical feature of the patient. In one non-limiting example, the anatomical feature of the patient may include a bone or a portion of a bone of the patient, such as a portion of a tibial bone, a femoral bone, and/or a patellar bone of the patient.

In a step 820, an anatomical 3D model 236 may be constructed based on the anatomical data 235 received. The anatomical 3D model 236 may represent the anatomical feature of the patient at the surgical site 320, 620. The anatomical 3D model 236 may include one or more anatomical features, which may include hard and/or soft tissues. The anatomical 3D model 236 may be constructed with any necessary level of accuracy. In some embodiments, only portions of objects may be represented in the anatomical 3D model 236. For example, for knee replacement surgery, only the distal end of the femur and/or the proximal end of the tibia may be represented in the anatomical 3D model 236. Performance of the step 820 may include using any of a wide variety of known techniques to generate 3D geometry based on the image data 232, the depth data 233, the spatial data 234, and/or the anatomical data 235. Attributes related to the anatomical 3D model 236 may include, but are not limited to: an exact or approximate morphology map of a patient's bone; an exact or approximate morphology map of a patient's bone with a desired resection morphology; an exact or approximate morphology map of a patient's bone with one or more drill holes formed in the anatomical 3D model; Data relating to specific locations, orientations, spacing, and/or sizes of access points, incisions, drill holes, at least two parallel pin holes to be formed in the bone and configured to receive at least two pins to secure a cutting guide to the bone; Data relating to resection cuts to be made in a bone or other tissues; Data relating to specific implant(s) and/or instrument size(s) and/or type(s) to be used, and/or the locations, orientations, or sizes of the implants as they will appear after implantation is complete, etc.

In a step 830, an image of the anatomical 3D model 236 may be projected on a head-mounted display unit 650 coupled to a surgeon, such that the projected image of the anatomical 3D model 236 is displayed within the surgeon's field-of-view on the head-mounted display unit 650 in an overlaid, spaced relationship relative to the exposed anatomical feature of the patient at the surgical site 320, 620. In this manner, the surgeon may simultaneously view the projected images overlaid on top of the actual exposed anatomical feature of the patient at the surgical site 320, 620 in an augmented reality environment. The projected images may include guidance information 238 derived from the surgical procedure plan that helps guide the surgeon through the surgical procedure. For example, the image may be projected onto translucent lenses 690 to indicate to the surgeon where to drill a hole in the exposed bone and/or indicate to the surgeon which portion(s) of the bone should be resected. The projected image may help the surgeon locate an access point to access the surgical site, facilitate the process of accessing the surgical site, carry out the surgical procedure, and/or assist in reconstruction of surrounding anatomy after completion of the main phase of the surgical procedure. Thus, the image may be projected in an overlaid fashion in augmented reality over soft tissue such as skin, over hard tissue such as bone, or even over non-anatomical elements such as other instruments involved in the surgical procedure. However, it will also be understood that other head-mounted display units utilizing virtual reality environments may also be used to create a surgical procedure plan.

In a step 840, one or more commands issued by the surgeon relative to the anatomical 3D model 236 may be sensed. The one or more commands may include, but are not limited to: a manual command that may be operated by hand (e.g., manually interacting with a device to control the device), a gaze command (e.g., performed with movement of the eyes/head), a gesture command (e.g., performed with the hands/fingers, such as an air tap, forming a closed fist, opening a closed fist, etc.), a voice command, and the like.

In a step 850, one or more attributes related to the anatomical 3D model 236 may be manipulated based on the one or more commands issued by the surgeon. Examples of different ways to manipulate the one or more attributes related to the anatomical 3D model 236 will be discussed below in more detail with respect to FIG. 9.

In a step 860, one or more desired attributes may be selected for inclusion in a surgical procedure plan that relate to the anatomical 3D model 236. Examples of attributes related to the anatomical 3D model 236 that may be selected include, but are not limited to: an exact or approximate morphology map of a patient's bone; an exact or approximate morphology map of a patient's bone with a desired resection morphology; an exact or approximate morphology map of a patient's bone with one or more drill holes formed in the anatomical 3D model 236; Data relating to specific locations, orientations, spacing, and/or sizes of access points, incisions, drill holes, at least two parallel pin holes to be formed in the bone and configured to receive at least two pins to secure a cutting guide to the bone; Data relating to resection cuts to be made in a bone or other tissues; Data relating to specific implant(s) and/or instrument size(s) and/or type(s) to be used, and/or the locations, orientations, or sizes of the implants as they will appear after implantation is complete, etc.

In a step 870, the surgical procedure plan may then be created based on the one or more desired attributes related to the anatomical 3D model that have been selected, and the method 800 may end.

In one particular example relating to knee replacement surgical procedures, one or more customized cutting guides may then be manufactured for the patient based on the patient-specific surgical procedure plan created by the surgeon. In this manner, the surgeon may be fully prepared to conduct a knee replacement surgery on the patient in accordance with the patient-specific surgical procedure plan and the customized cutting guides that have been manufactured based on the specific morphology of the patient derived from the patient-specific surgical procedure plan.

The various steps of the method 800, or any other method disclosed herein, may be reordered, omitted, and/or replaced with different steps within the scope of the present disclosure. Those of skill in the art, with the aid of the present disclosure, will recognize that many variations may be made to the method 800, or any other method disclosed herein, depending on the particular surgical procedure to be carried out, as well as the configuration of the system used in the performance of that surgical procedure.

Figure 9:
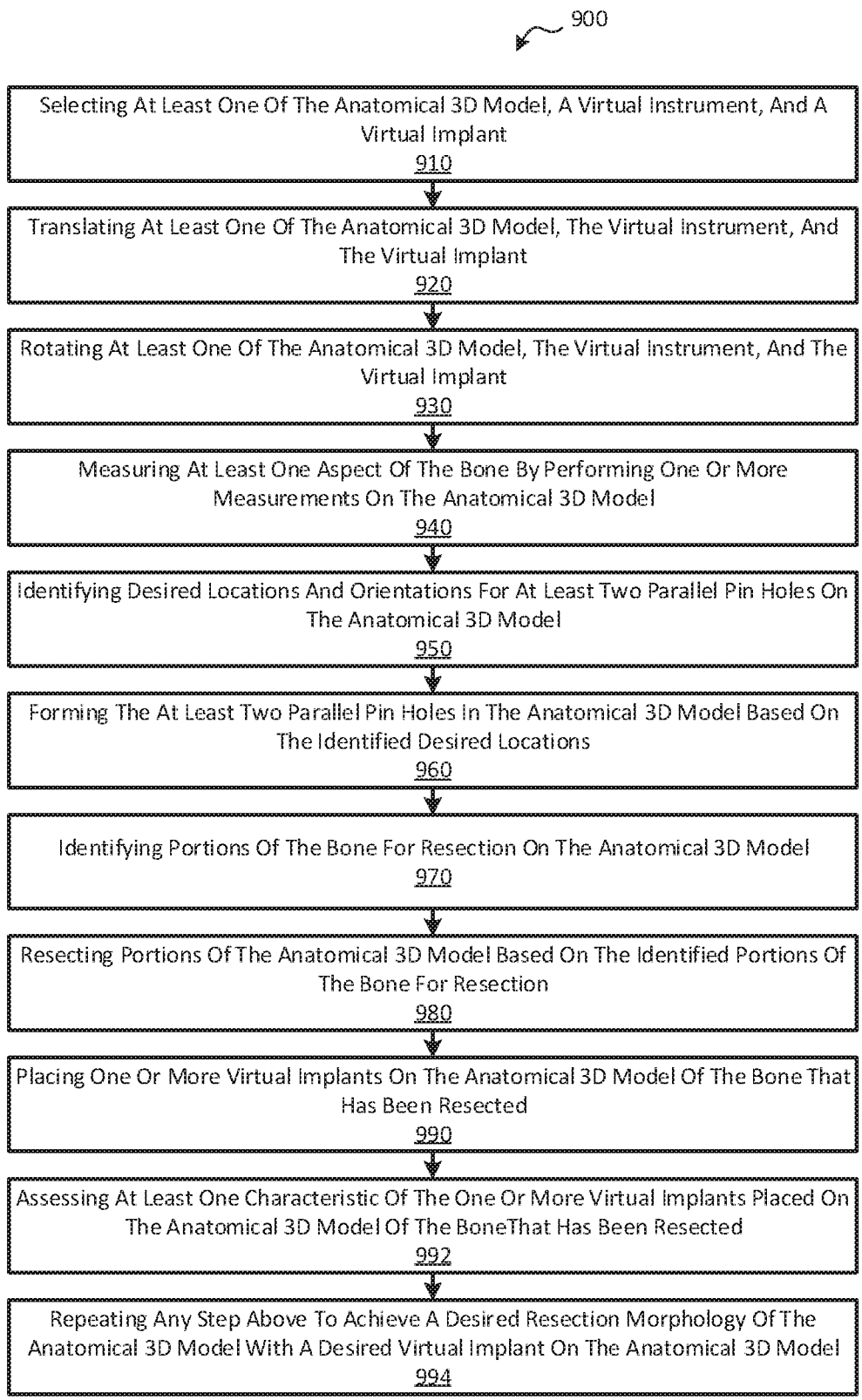
FIG. 9 is a flowchart diagram illustrating a method for manipulating one or more attributes related to an anatomical 3D model, according to one embodiment of the disclosure.

FIG. 9 is a flowchart diagram illustrating a method 900 for manipulating one or more attributes related to an anatomical 3D model 236 (as in the step 850 of FIG. 8, as one example), according to one embodiment of the disclosure. The method 900 will be described in connection with the head-mounted display unit 650 shown in FIG. 6. However, those of skill in the art will recognize that alternative systems may also be used in the performance of the method 900, and the head-mounted display unit 650 may also be utilized in connection with alternative methods. For example, although the head-mounted display unit 650 shown in FIG. 6 utilizes an augmented reality environment (due to the use of translucent lenses 690), other head-mounted display units utilizing virtual reality environments may also be used.

The method 900 describes various steps in which one or more attributes related to an anatomical 3D model 236 representing a bone of a patient may be manipulated. For example, the method 900 may begin with a step 910 in which the one or more attributes related to the anatomical 3D model 236 may be manipulated by selecting at least one of the anatomical 3D model 236, a virtual instrument, and a virtual implant within the augmented reality environment. A surgeon may utilize a suitable command to select the anatomical 3D model 236, the virtual instrument, and/or the virtual implant, such as a manual hand-operated command, a gaze command, a gesture command, a voice command, and the like.

In a step 920, the one or more attributes related to the anatomical 3D model 236 may be further manipulated by translating at least one of the anatomical 3D model 236, the virtual instrument, and/or the virtual implant after they have been selected within the augmented reality environment. The surgeon may similarly utilize any suitable command to translate the anatomical 3D model 236, the virtual instrument, and/or the virtual implant, such as a manual hand-operated command, a gaze command, a gesture command, a voice command, and the like.

In a step 930, the one or more attributes related to the anatomical 3D model 236 may be further manipulated by rotating at least one of the anatomical 3D model 236, the virtual instrument, and/or the virtual implant after they have been selected within the augmented reality environment. The surgeon may similarly utilize any suitable command to rotate the anatomical 3D model 236, the virtual instrument, and/or the virtual implant, such as a manual hand-operated command, a gaze command, a gesture command, a voice command, and the like.

In a step 940, the one or more attributes related to the anatomical 3D model 236 may be further manipulated by performing one or more measurements on the anatomical 3D model 236 within the augmented reality environment in order to ascertain one or more measurements of the actual anatomical feature of the patient.

In a step 950, the one or more attributes related to the anatomical 3D model 236 may be further manipulated within the augmented reality environment by identifying desired locations and orientations for at least two parallel pin holes on the anatomical 3D model 236 in order to simulate placement of a cutting guide during surgery. The at least two parallel pin holes may be sized, oriented, and spaced apart to receive at least two pins within the at least two parallel pin holes in order to secure the cutting guide to the bone during surgery.

In a step 960, the one or more attributes related to the anatomical 3D model 236 may be further manipulated within the augmented reality environment by forming the at least two parallel pin holes in the anatomical 3D model 236 based on the identified desired locations from step 950.

In a step 970, the one or more attributes related to the anatomical 3D model 236 may be further manipulated within the augmented reality environment by identifying portions of the bone for resection on the anatomical 3D model 236.

In a step 980, the one or more attributes related to the anatomical 3D model 236 may be further manipulated within the augmented reality environment by resecting portions of the anatomical 3D model 236 based on the identified portions of the bone for resection from step 970, in order to simulate and/or plan the resection of portions of the bone during surgery.

In a step 990, the one or more attributes related to the anatomical 3D model 236 may be further manipulated within the augmented reality environment by placing one or more virtual implants on the anatomical 3D model 236 of the bone after the bone has been resected in the step 980.

In a step 992, the one or more attributes related to the anatomical 3D model 236 may be further manipulated within the augmented reality environment by assessing at least one characteristic of the one or more virtual implants placed on the anatomical 3D model 236 of the bone that has been resected. This may include performing further measurements or analysis of least one characteristic of the one or more virtual implants placed on the anatomical 3D model 236 of the bone that has been resected, in order to determine whether or not the one or more virtual implants placed on the anatomical 3D model 236 appear to suitably fit the patient.

In a step 994, the one or more attributes related to the anatomical 3D model 236 may be further manipulated within the augmented reality environment by iteratively repeating any of the above steps 910 through 992 in order to achieve a desired resection morphology of the anatomical 3D model 236 in combination with a desired virtual implant placed on the anatomical 3D model 236. In this manner, a desired virtual implant having a desired sizing, placement, fitment, and functionality relative to the anatomical 3D model 236 may be achieved, and the method 900 may end.

The various steps of the method 900 may be reordered, omitted, and/or replaced with different steps within the scope of the present disclosure. Those of skill in the art, with the aid of the present disclosure, will recognize that many variations may be made to the method 900 depending on the particular surgical procedure to be carried out, as well as the configuration of the system used in the performance of that surgical procedure. Moreover, any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A system for guiding a surgical procedure based on a surgical procedure plan, the system comprising:
   at least one image capture device configured to capture at least one image of an exposed anatomical feature of a patient at a surgical site;
   a computing device configured to:
      receive a surgical procedure plan, the surgical procedure plan based on one or more desired attributes related to an anatomical 3D model that represents the exposed anatomical feature of the patient at the surgical site; and
      register the anatomical 3D model to the exposed anatomical feature of the patient based on the at least one image of the exposed anatomical feature; and
   at least one projector configured to provide guidance information to a surgeon based on the surgical procedure plan to facilitate performance of the surgical procedure at the surgical site by the surgeon.

2. The system of claim 1, wherein:
   the at least one image capture device is coupled to a surgical tool;
   the at least one projector is coupled to the surgical tool; and
   the at least one projector is configured to project light onto the exposed anatomical feature of the patient at the surgical site to guide the surgeon through the surgical procedure.

3. The system of claim 2, wherein:
   the exposed anatomical feature of the patient at the surgical site is an exposed portion of a bone of the patient and the anatomical 3D model is representative of the exposed portion of the bone;
   the surgical procedure plan identifies desired locations and orientations for at least two parallel pin holes to be formed in the exposed portion of the bone based on the anatomical 3D model;
   the at least two parallel pin holes are sized, oriented, and spaced apart to receive at least two pins to secure a cutting guide to the exposed portion of the bone; and
   the at least one projector is configured to project light onto the exposed portion of the bone to indicate the desired locations for the at least two parallel pin holes to be formed in the exposed portion of the bone.

4. The system of claim 1, wherein:
   the at least one image capture device is coupled to a head-mounted display unit;
   the at least one projector is coupled to the head-mounted display unit; and
   the at least one projector is configured to project images onto at least one translucent lens coupled to the head-mounted display unit in order to display the projected images within a surgeon's field-of-view in an overlaid spaced relationship relative to the exposed anatomical feature of the patient at the surgical site in order to guide the surgeon through the surgical procedure.

5. The system of claim 4, wherein:
   the exposed anatomical feature of the patient at the surgical site is an exposed portion of a bone of the patient and the anatomical 3D model is representative of the exposed portion of the bone;
   the surgical procedure plan identifies desired locations and orientations for at least two parallel pin holes to be formed in the exposed portion of the bone based on the anatomical 3D model;
   the at least two parallel pin holes are sized, oriented, and spaced apart to receive at least two pins to secure a cutting guide to the exposed portion of the bone; and
   the at least one projector is configured to project images onto the at least one translucent lens to indicate the desired locations and orientations for the at least two parallel pin holes to be formed in the exposed portion of the bone.

6. The system of claim 5, further comprising an audio device that produces a sound that indicates whether a drill tool is properly aligned with the desired locations and orientations of the at least two parallel pin holes to be formed in the exposed portion of the bone.

7. The system of claim 4, wherein the head-mounted display unit further comprises at least one of: a photographic video camera, a 3D camera, a depth sensing camera, an environment mapping camera, an infrared camera, a light-field camera, a plenoptic light-field camera, a time of flight sensor, a LiDAR sensor, an ambient light sensor, a proximity sensor, an eye-tracking sensor, a head-tracking sensor, an accelerometer, a gyroscope, and a magnetometer.

8. A method for guiding a surgical procedure based on a surgical procedure plan, the method comprising:
receiving a surgical procedure plan, the surgical procedure plan based on one or more desired attributes related to an anatomical 3D model representing an anatomical feature of a patient at a surgical site;
capturing at least one image of an exposed anatomical feature of the patient at the surgical site;
registering the anatomical 3D model to the exposed anatomical feature of the patient at the surgical site; and
providing guidance information to a surgeon based on the surgical procedure plan to facilitate performance of the surgical procedure at the surgical site by the surgeon.

9. The method of claim 8, wherein:
capturing the at least one image of the exposed anatomical feature of the patient at the surgical site is performed by at least one image capture device coupled to a surgical tool;
providing guidance information to the surgeon based on the surgical procedure plan is performed by at least one projector coupled to the surgical tool; and
the at least one projector is configured to project light onto the exposed anatomical feature of the patient at the surgical site to guide the surgeon through the surgical procedure.

10. The method of claim 9, wherein:
the exposed anatomical feature of the patient at the surgical site is an exposed portion of a bone of the patient and the anatomical 3D model is representative of the exposed portion of the bone;
the surgical procedure plan identifies desired locations and orientations for at least two parallel pin holes to be formed in the bone based on the anatomical 3D model;
the at least two parallel pin holes are sized, oriented, and spaced apart to receive at least two pins to secure a cutting guide to the exposed portion of the bone; and
the at least one projector is configured to project light onto the exposed portion of the bone to indicate the desired locations for the at least two parallel pin holes to be formed in the exposed portion of the bone.

11. The method of claim 8, wherein:
capturing the at least one image of the exposed anatomical feature of the patient at the surgical site is performed by at least one image capture device coupled to a head-mounted display unit;
providing guidance information to the surgeon based on the surgical procedure plan is performed by at least one projector coupled to the head-mounted display unit; and
the at least one projector is configured to project images onto at least one translucent lens coupled to the head-mounted display unit in order to display the projected images within a surgeon's field-of-view in an overlaid spaced relationship relative to the exposed anatomical feature of the patient at the surgical site in order to guide the surgeon through the surgical procedure.

12. The method of claim 11, wherein:
the exposed anatomical feature of the patient at the surgical site is an exposed portion of a bone of the patient, and the anatomical 3D model is representative of the exposed portion of the bone;
the surgical procedure plan identifies desired locations and orientations for at least two parallel pin holes to be formed in the exposed portion of the bone based on the anatomical 3D model;
the at least two parallel pin holes are sized, oriented, and spaced apart to receive at least two pins to secure a cutting guide to the exposed portion of the bone; and
the at least one projector is configured to project images onto the at least one translucent lens to indicate the desired locations and orientations for the at least two parallel pin holes to be formed in the exposed portion of the bone.

13. The method of claim 12, wherein providing guidance information to the surgeon based on the surgical procedure plan further comprises emitting an audible sound to indicate when a drill tool is properly aligned with the desired locations and orientations of the at least two parallel pin holes to be formed in the exposed portion of the bone.

14. The method of claim 11, wherein the head-mounted display unit further comprises at least one of: a photographic video camera, a 3D camera, a depth sensing camera, an environment mapping camera, an infrared camera, a light-field camera, a plenoptic light-field camera, a time of flight sensor, a LiDAR sensor, an ambient light sensor, a proximity sensor, an eye-tracking sensor, a head-tracking sensor, an accelerometer, a gyroscope, and a magnetometer.

15. A method for creating a surgical procedure plan, the method comprising:
receiving anatomical data indicative of an anatomical feature of a patient at a surgical site;
constructing an anatomical 3D model based on the anatomical data, the anatomical 3D model representing the anatomical feature of the patient at the surgical site;
projecting an image of the anatomical 3D model on a head-mounted display unit coupled to a surgeon, such that the projected image of the anatomical 3D model is displayed within a surgeon's field-of-view on the head-mounted display unit;
sensing one or more commands issued by the surgeon relative to the anatomical 3D model;
manipulating one or more attributes related to the anatomical 3D model based on the one or more commands issued by the surgeon;
selecting one or more desired attributes related to the anatomical 3D model for inclusion in a surgical procedure plan; and
creating the surgical procedure plan based on the selected one or more desired attributes related to the anatomical 3D model.

16. The method of claim 15, wherein the anatomical data comprises at least one of: CT scan data, MRT data, MRI data, 2D x-ray data, and 3D x-ray data.

17. The method of claim 15, wherein the head-mounted display unit displays the anatomical 3D model to the surgeon in at least one of an augmented reality environment and a virtual reality environment.

18. The method of claim 15, wherein the head-mounted display unit comprises at least one of: a projector, a photographic video camera, a 3D camera, a depth sensing camera, an environment mapping camera, an infrared camera, a light-field camera, a plenoptic light-field camera, a time of flight sensor, a LiDAR sensor, an ambient light sensor, a proximity sensor, an eye-tracking sensor, a head-tracking sensor, an accelerometer, a gyroscope, and a magnetometer.

19. The method of claim 15, wherein the one or more commands comprises at least one of: a gaze command, a gesture command, and a voice command.

20. The method of claim 15, wherein the anatomical 3D model represents a bone of the patient and manipulating the one or more attributes related to the anatomical 3D model comprises at least one of:
- selecting at least one of the anatomical 3D model, a virtual instrument, and a virtual implant;
- translating at least one of the anatomical 3D model, the virtual instrument, and the virtual implant;
- rotating at least one of the anatomical 3D model, the virtual instrument, and the virtual implant;
- measuring at least one aspect of the bone by performing one or more measurements on the anatomical 3D model;
- identifying desired locations and orientations for at least two parallel pin holes on the anatomical 3D model in order to simulate placement of a cutting guide during surgery, the at least two parallel pin holes being sized, oriented, and spaced apart to receive at least two pins within the at least two parallel pin holes in order to secure the cutting guide to the bone during surgery;
- forming the at least two parallel pin holes in the anatomical 3D model based on the identified desired locations;
- identifying portions of the bone for resection on the anatomical 3D model;
- resecting portions of the anatomical 3D model based on the identified portions of the bone for resection in order to simulate resection of portions of the bone during surgery;
- placing one or more virtual implants on the anatomical 3D model of the bone that has been resected;
- assessing at least one characteristic of the one or more virtual implants placed on the anatomical 3D model of the bone that has been resected; and
- repeating any step above in order to achieve a desired resection morphology of the anatomical 3D model combined with a desired virtual implant placed on the anatomical 3D model, the desired virtual implant having a desired sizing, placement, fitment, and functionality relative to the anatomical 3D model that has been resected.

* * * * *